(12) United States Patent
Gemperli et al.

(10) Patent No.: US 10,730,918 B2
(45) Date of Patent: Aug. 4, 2020

(54) TRAP 63

(71) Applicant: STRAUMANN HOLDING AG, Basel (CH)

(72) Inventors: Anja C. Gemperli, Basel (CH); Oleh Andrukhov, Deutsch Wagram (AT)

(73) Assignee: STRAUMANN HOLDING AG, Basel (CH)

( * ) Notice: Subject to any disclaimer, the term of this patent is extended or adjusted under 35 U.S.C. 154(b) by 596 days.

(21) Appl. No.: 14/787,941

(22) PCT Filed: Apr. 30, 2014

(86) PCT No.: PCT/EP2014/058796
§ 371 (c)(1),
(2) Date: Oct. 29, 2015

(87) PCT Pub. No.: WO2014/177602
PCT Pub. Date: Nov. 6, 2014

(65) Prior Publication Data
US 2016/0068579 A1 Mar. 10, 2016

Related U.S. Application Data

(60) Provisional application No. PCT/EP2014/058796, filed on Apr. 30, 2014.

(30) Foreign Application Priority Data

Apr. 30, 2013 (SE) ...................................... 1350528

(51) Int. Cl.
| | | |
|---|---|---|
| C07K 14/47 | (2006.01) |
| A61K 35/32 | (2015.01) |
| A61K 38/39 | (2006.01) |
| C07K 14/78 | (2006.01) |
| A61K 38/00 | (2006.01) |

(52) U.S. Cl.
CPC .............. *C07K 14/47* (2013.01); *A61K 35/32* (2013.01); *A61K 38/39* (2013.01); *C07K 14/78* (2013.01); *A61K 38/00* (2013.01)

(58) Field of Classification Search
CPC ........ C07K 14/47; A61K 35/32; A61K 38/39; A61K 38/1709
See application file for complete search history.

(56) References Cited

U.S. PATENT DOCUMENTS

2002/0169105 A1* 11/2002 Gestrelius ................ A61K 8/19
424/549
2007/0010893 A1 1/2007 Wen et al.

FOREIGN PATENT DOCUMENTS

| WO | WO2006/101411 A2 | 9/2006 |
| WO | WO2009/157869 A1 | 12/2009 |
| WO | WO2011/073447 A1 | 6/2011 |
| WO | WO2011/073447 A9 | 6/2011 |
| WO | WO2011/077086 A2 | 6/2011 |
| WO | WO2011/077086 A3 | 6/2011 |

OTHER PUBLICATIONS

UniProt entry Q9TQY2_PIG, May 1, 2000.*
UniProt entry F6PLF2_CANLF, Oct. 31, 2012.*
UniProt entry F1MYJ0_BOVIN, May 3, 2011.*
Lyngstadaas et al. ("Enamel matrix proteins; old molecules for new applications," Orthod Craniofac Res. Aug. 2009 ; 12(3): 243-253) (Year: 2009).*
Accession Nr. AZJ08722, Hämtat fr dgene 2851, 2013.
Accession Nr. AEN03411, hämtat från dgene 2852, 2013.
Accession Nr. AEK64129, hämtat från dgene 2853, 2013.
International Search Report and Written Opinion for PCT Patent App. No. PCT/EP2014/058796 (dated Jul. 29, 2014).

* cited by examiner

*Primary Examiner* — Christina Bradley
(74) *Attorney, Agent, or Firm* — Cermak Nakajima & McGowan LLP; Malcolm K. McGowan

(57) ABSTRACT

The present invention for the first time discloses a novel small molecular weight enamel matrix polypeptide which is at least 80%, such as 90% identical to the amino acid sequence as shown in SEQ ID NO: 1 (MPLPPHPGHP GYINFSYEVL TPLKWYQNMI RHPYTSYGYE PMGG-WLHHQI IPWSQQTPQ SHA) (TRAP63), a homologue, analogue, or a pharmaceutically acceptable salt thereof. The present invention further discloses a pharmaceutical composition consisting of an enamel matrix polypeptide which is at least 80%, such as 90% identical to the amino acid sequence as shown in SEQ ID NO: 1, a homologue, analogue, or a pharmaceutically acceptable salt thereof, and a suitable pharmaceutical carrier, which further can consist of one or more enamel matrix polypeptides selected from the group of enamel matrix polypeptides which correspond to: a. SEQ ID NO: 2, b. SEQ ID NO: 3 and c. SEQ ID NO: 4.

Figure 1:
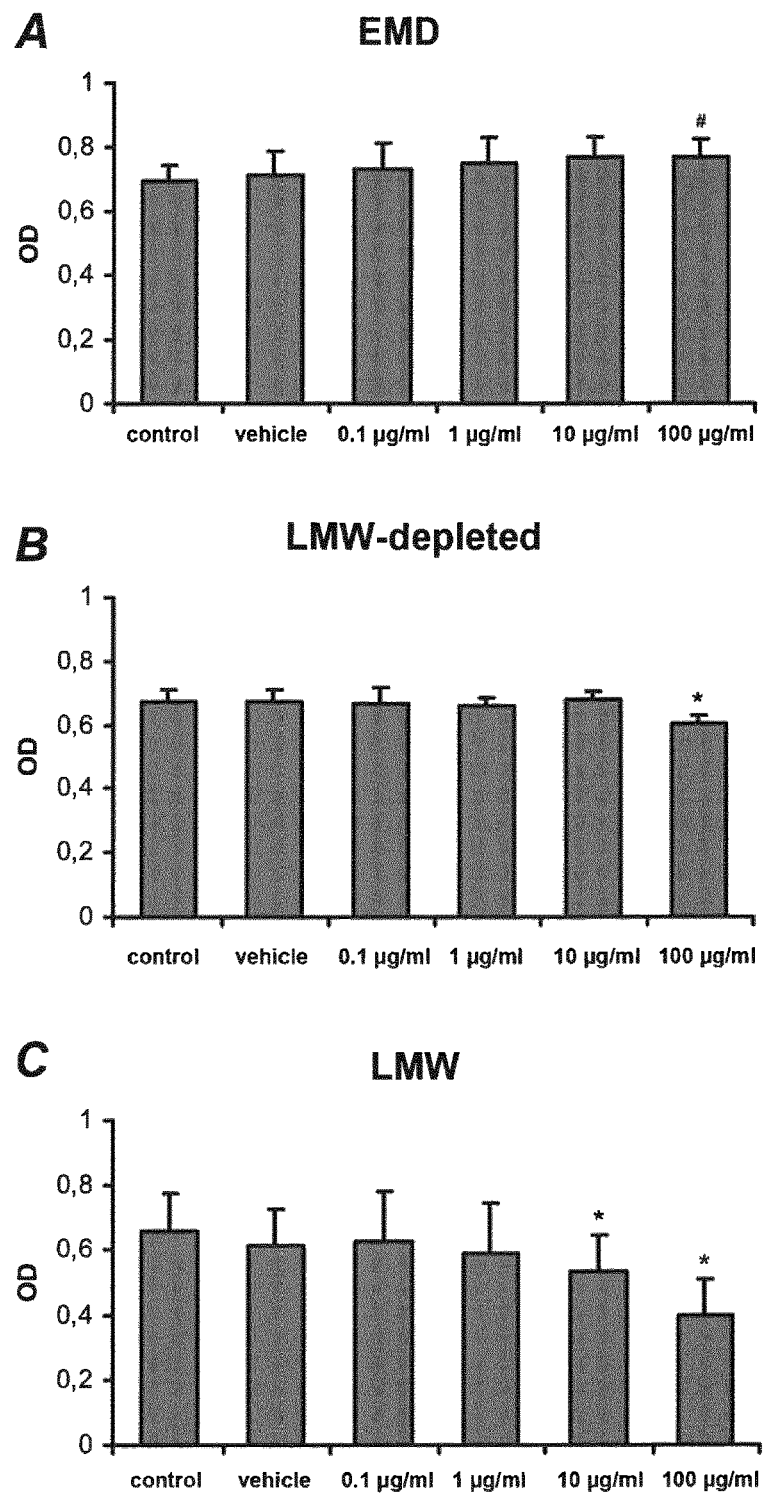

17 Claims, 17 Drawing Sheets
Specification includes a Sequence Listing.

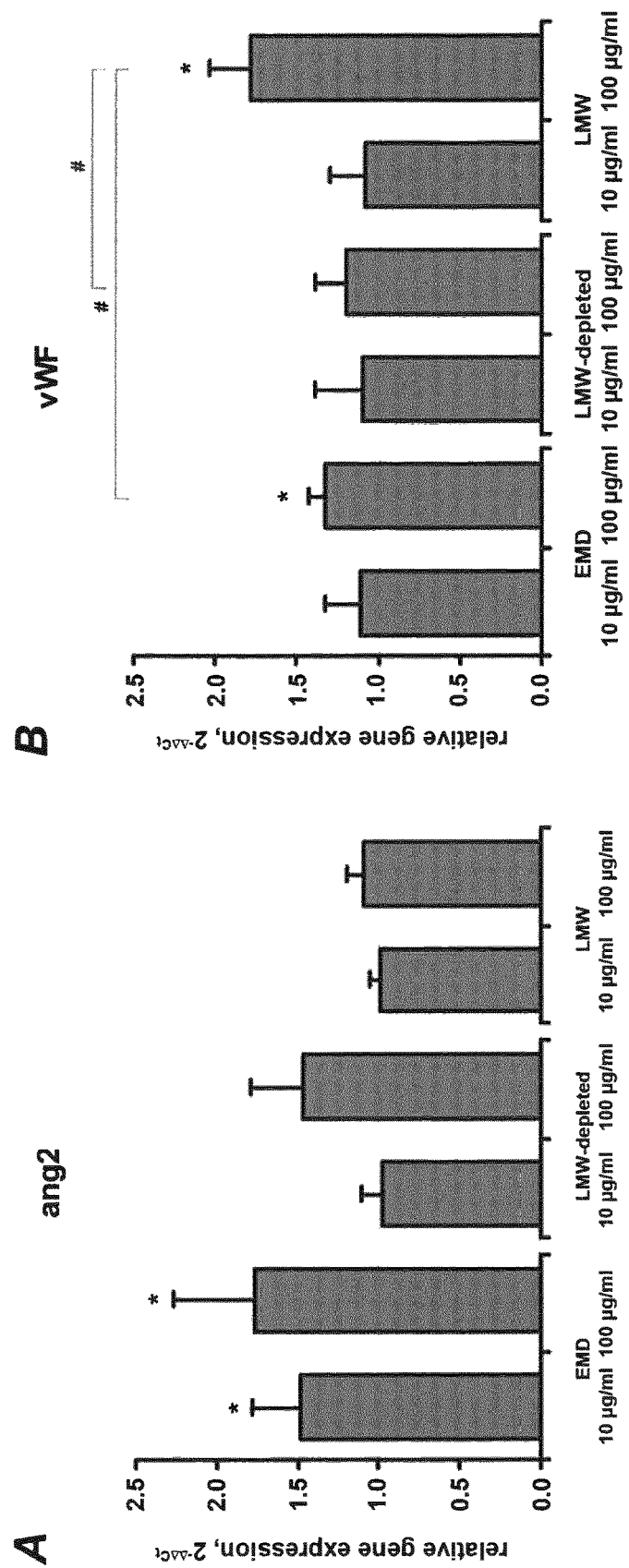
Fig. 4A/B

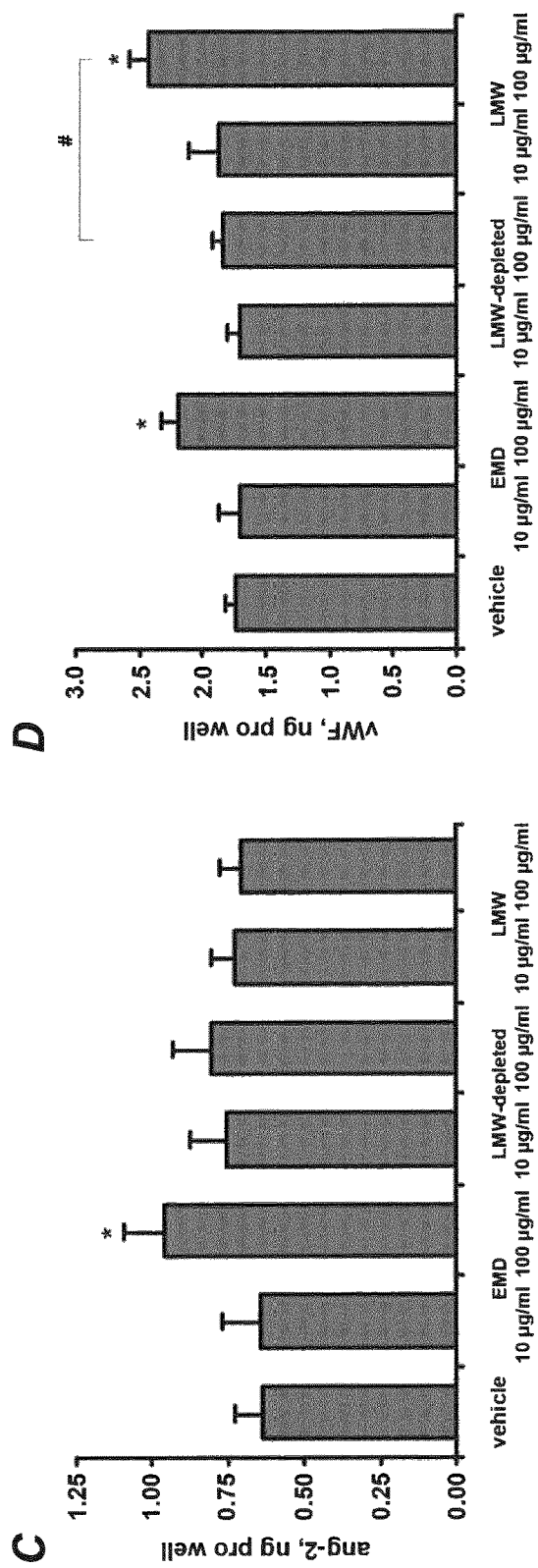
Fig. 4C/D

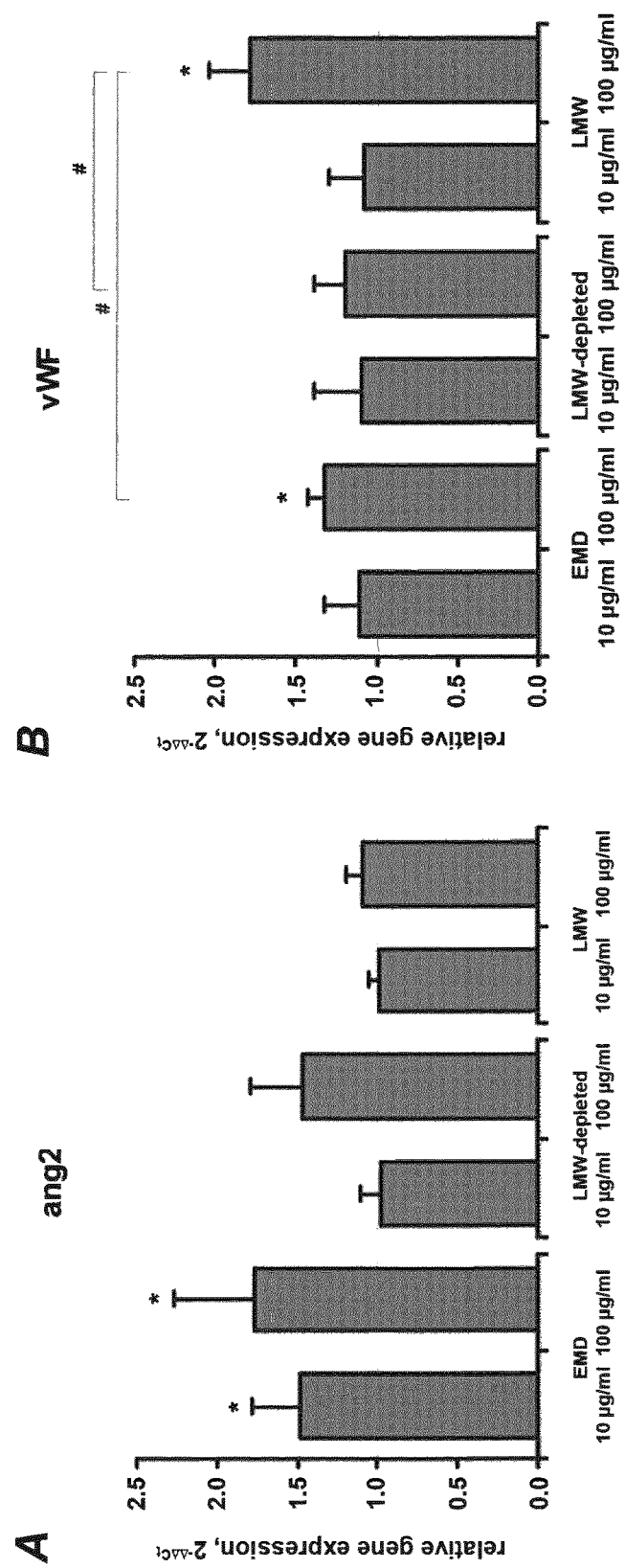
Fig. 5 A/B

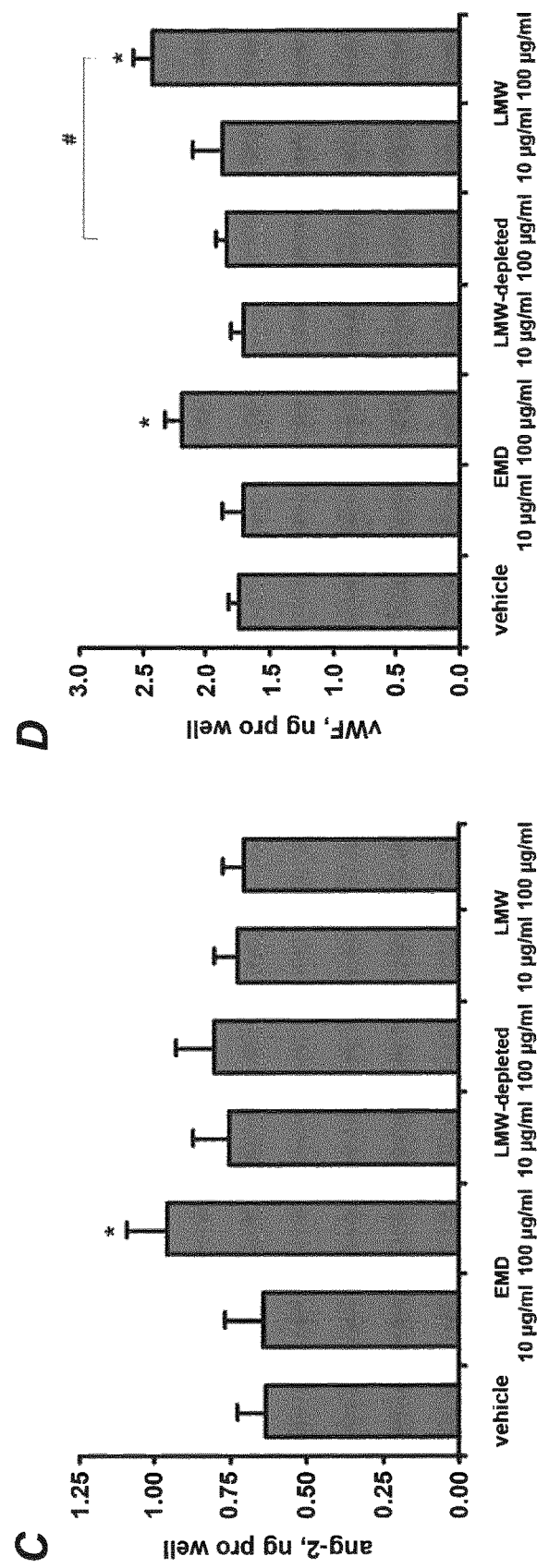
Fig. 5 C/D

SEQUENCE LISTING

<160> NUMBER OF SEQ ID NOS: 4

<210> SEQ ID NO 1
<211> LENGTH: 63
<212> TYPE: PRT
<213> ORGANISM: Sus scrofa domesticus

<400> SEQUENCE: 1

Met Pro Leu Pro Pro His Pro Gly His Pro Gly Tyr Ile Asn Phe Ser
1               5                   10                  15

Tyr Glu Val Leu Thr Pro Leu Lys Trp Tyr Gln Asn Met Ile Arg His
            20                  25                  30

Pro Tyr Thr Ser Tyr Gly Tyr Glu Pro Met Gly Gly Trp Leu His His
        35                  40                  45

Gln Ile Ile Pro Val Val Ser Gln Gln Thr Pro Gln Ser His Ala
    50                  55                  60

<210> SEQ ID NO 2
<211> LENGTH: 43
<212> TYPE: PRT
<213> ORGANISM: sus scrofa domesticus

<400> SEQUENCE: 2

Met Pro Leu Pro Pro His Pro Gly His Pro Gly Tyr Ile Asn Phe Ser
1               5                   10                  15

Tyr Glu Val Leu Thr Pro Leu Lys Trp Tyr Gln Asn Met Ile Arg His
            20                  25                  30

Pro Tyr Thr Ser Tyr Gly Tyr Glu Pro Met Gly
        35                  40

<210> SEQ ID NO 3
<211> LENGTH: 45
<212> TYPE: PRT
<213> ORGANISM: sus scrofa domesticus

<400> SEQUENCE: 3

Met Pro Leu Pro Pro His Pro Gly His Pro Gly Tyr Ile Asn Phe Ser
1               5                   10                  15

Tyr Glu Val Leu Thr Pro Leu Lys Trp Tyr Gln Asn Met Ile Arg His
            20                  25                  30

Pro Tyr Thr Ser Tyr Gly Tyr Glu Pro Met Gly Gly Trp
        35                  40                  45

<210> SEQ ID NO 4
<211> LENGTH: 56
<212> TYPE: PRT
<213> ORGANISM: sus scrofa domesticus

<400> SEQUENCE: 4

Met Pro Leu Pro Pro His Pro Gly His Pro Gly Tyr Ile Asn Phe Ser
1               5                   10                  15

Tyr Glu Val Leu Thr Pro Leu Lys Trp Tyr Gln Asn Met Ile Arg His
            20                  25                  30

Pro Ser Leu Leu Pro Asp Leu Pro Leu Glu Ala Trp Pro Ala Thr Asp
        35                  40                  45

Lys Thr Lys Arg Glu Glu Val Asp
    50                  55

TRAP 63

CONTINUING APPLICATION DATA

This application is a national stage filing under 35 USC 371 of PCT/EP2014/058796, filed 13 Apr. 2014, which claims priority from Swedish application SE 1350528-4, filed 30 Apr. 2013. The contents of these prior applications are incorporated herein in their entirety by reference.

FIELD OF THE INVENTION

The present invention relates to the field of enamel matrix proteins and to the use of them in wound healing. In particular, the invention relates to the disclosure of a new active amelogenin polypeptide ((SEQ.ID.NO: 1) TRAP 63) that in particular stimulates the tissue formation phase of a wound healing process.

BACKGROUND OF THE INVENTION

Enamel matrix proteins, present in the enamel matrix, are most well-known as precursors to enamel. Prior to cementum formation, enamel matrix proteins are deposited on the root surface at the apical end of the developing tooth-root. There is evidence that the deposited enamel matrix is the initiating factor for the formation of cementum. Again, the formation of cementum in itself is associated with the development of the periodontal ligament and the alveolar bone. Enamel matrix proteins can therefore promote periodontal regeneration through mimicking the natural attachment development in the tooth (Gestrelius S, Lyngstadaas S P, Hammarstrøm L. Emdogain—periodontal regeneration based on biomimicry. Clin Oral Invest 4:120-125 (2000)).

Isolated enamel matrix proteins are able to induce not only one but an orchestrated cascade of factors, naturally found in tissues developing adjacent to the enamel matrix They mimic the natural environment of a developing tissue and thus mimic a natural stimulation for tissue regeneration, cell differentiation and/or maturation.

Enamel matrix derivative (EMD), in the form of a purified acid extract of proteins from pig enamel matrix, has previously been successfully employed to restore functional periodontal ligament, cementum and alveolar bone in patients with severe tooth attachment loss (Hammarstrøm et al., 1997, Journal of Clinical Periodontology 24, 658-668).

Furthermore, in studies on cultured periodontal ligament cells (PDL), it was shown that the attachment rate, growth and metabolism of these cells were significantly increased when EMD was present in the cultures. Also, cells exposed to EMD showed increased intracellular cAMP signalling and autocrine production of growth factors, when compared to controls. Epithelial cells on the other hand, although increasing cAMP signalling and growth factor secretion when EMD was present, were inhibited in both proliferation and growth (Lyngstadaas et al., 2001, Journal of Clinical Periodontology 28, 181-188).

Enamel matrix proteins and enamel matrix derivatives (EMD) have previously been described in the patent literature to be able to induce hard tissue formation (i.e. enamel formation, U.S. Pat. No. 4,672,032 (Slavkin)), endorse binding between hard tissues (EP-B-0 337 967 and EP-B-0 263 086), promote open wound healing, such as of skin and mucosa, have a beneficial effect on treatment of infections and inflammatory diseases (EP-1059934 and EP-01201915.4), induce regeneration of dentin (WO 01/97834), promote the take of a graft (WO 00/53197), induce apoptosis in the treatment of neoplasms (WO 00/53196), regulate imbalance in an immune response to a systemic infection or inflammation (WO 03/024479), and to facilitate filling a wound cavity and/or tissue defect following from a procedure and/or trauma, such as a cytoreductive surgery (WO 02/080994).

The enamel matrix is composed of a number of proteins, such as amelogenins, enamelin, tuft protein, proteases, and albumin. Amelogenins, a major constituent of the enamel matrix, are a family of hydrophobic proteins derivable from a single gene by alternative splicing and controlled post secretory processing. They are highly conserved throughout vertebrate evolution and demonstrate a high overall level of sequence homology among all higher vertebrates examined (80%). In fact, the sequences of porcine and human amelogenin gene transcript differ only in 4% of the bases (i.e. they are approximately 90-96% identical). Thus, enamel matrix proteins, although of porcine origin, are considered "self" when encountered in the human body and can promote dental regeneration in humans without triggering allergic responses or other undesirable reactions. Nonetheless, the plurality of structures identified in the different amelogenins studied, that will even occur in the same individual animal or human dentitions, clearly gives rise to speculations on the extreme specificity of the structures that work in concert in a "normal" amelogenesis. E.g., a single base mutation in the x-chromosomal amelogenin gene, which results in a single proline to threonine change in the expressed human amelogenin, does give rise to amelogenesis imperfecta.

During cementogenesis in the developing tooth, amelogenin degrades into smaller pieces, and these pieces seem to interact differentially with the surrounding tissue and promote serial steps in the development of the periodontal system. As already described in Fincham et al, 1993, enamel contains a complex of amelogenin proteins which includes components ranging in size from 5-25 kDa. This is due to the expression and secretion of a family of amelogenins derivable from multiple mRNAs generated by differential splicing from one or two copies of the amelogenin gene, located on the X and Y chromosome. What is more, subsequent to secretion, these proteins appear further to undergo extensive proteolytic processing. Because of this extensive alternative splicing of the primary transcript and the following proteolytic processing of the secreted proteins, it has been difficult to assign functions to individual amelogenins. The pattern of splicing is unique for each amelogenin gene yet investigated, even when two copies of the gene are expressed in the same cell. Despite the high conservation of amelogenin sequences across species, diversity in the pattern of RNA splicing thus leads to significant differences in the number and character of amelogenin isoforms in the developing enamel matrix.

The need for a more refined use of enamel matrix protein, e.g. to induce specific steps during periodontal development, such as de novo bone formation or cementogenesis, or to mimic them in medical treatments has long been felt in the field. The need for an efficient possibility to synthesize single defined polypeptide sequences for use as separate and/or combined active components for inducing a specific desired effect has long been sought for, but, due to the complexity of the endogenous expression and processing of amelogenin proteins, attempts at separation of certain closely defined fractions and/or polypeptides or fragments of polypeptides from e.g. porcine tissues with specific biological activities have meet with severe obstacles.

To date, two classes of amelogenin proteins have been described in the size of between 5-6 kDa, namely leucinerich amelogenin polypeptide (LRAP) and tyrosine-rich amelogenin polypeptide (TRAP). LRAP is translated from a shorter mRNA that has the coding regions from exons 4, 5 and part of 6 deleted during splicing. Due to its potential important regulatory effect as one of the processed fragments found of amelogenin, it was 2004 investigated by Boabaid et al, (Boabaid F., et al, J. Periodontol, Vol 75, No. 8, 2004) but was reported not to have any effect on cell proliferation in itself. What is more, it decreased the number of cementoblasts in cell culture, contrary to EMD which promotes cell proliferation of cementoblasts in vitro and full length amelogenin, which has no reported effect.

Two human tyrosine-rich amelogenin polypeptides (TRAPs) of approximately 5 kDa in size have prior been identified (see Fincham et al., 1989). These polypeptides were found to be of 42 (TRAP-2) and 44 (TRAP-1) amino acid residues in length; two forms of TRAP molecules, differing only by cleavage of a carboxy-terminal dipeptide, which were described to be a general feature of human and other mammalian enamel proteins, probably being derived by postsecretory cleavage from the primary extracellular amelogenin. No specific biological effect has so far been attributed to these polypeptides either. In WO 2009/157869, the present inventors finally were able to describe 2 naturally occurring porcine N-terminal amelogenin polypeptide fragments that together were shown to be able to induce osteogenic activity, such as proliferation of precursor cells and early differentiation of osteoblasts (TRAP 43 and TRAP 45).

The present invention now for the first time discloses all components of a newly identified low molecular weight fraction of isolated enamel matrix derivatives that can clearly be shown to be more effective in reducing the inflammatory response in a targeted soft tissue than the complete enamel matrix extract (EMD). In particular, one specific polypeptide is identified that has been prior unknown and which stimulates the tissue formation phase of the wound healing process. Its use is herein described in promoting and/or improving soft tissue regeneration and/or stimulation of angiogenesis, such as in periodontal tissues.

DISCLOSURE OF THE INVENTION

The present invention for the first time discloses a novel small molecular weight enamel matrix polypeptide which is at least 80%, such as 90% identical to the amino acid sequence as shown in SEQ ID NO: 1 (MPLPPHPGHP GYINFSYEVL TPLKWYQNMI RHPYTSYGYE PMGGWLHHQI IPWSQQTPQ SHA), a homologue, analogue, or a pharmaceutically acceptable salt thereof, which can stimulate the tissue formation phase of a wound healing process. The novel small molecular weight enamel matrix polypeptide corresponding to the amino acid sequence shown in SEQ ID NO: 1 is in the present context referred to as TRAP63.

The present invention further discloses a pharmaceutical composition consisting of an enamel matrix polypeptide which is at least 80%, such as 90% identical to the amino acid sequence as shown in SEQ ID NO: 1 (MPLPPHPGHP GYINFSYEVL TPLKWYQNMI RHPYTSYGYE PMGG-WLHHQI IPWSQQTPQ SHA) (TRAP63), a homologue, analogue, or a pharmaceutically acceptable salt thereof, which can stimulate the tissue formation phase of a wound healing process, and a suitable pharmaceutical carrier.

Further again, the present invention discloses a pharmaceutical composition consisting of an enamel matrix polypeptide which is at least 80%, such as 90% identical to the amino acid sequence as shown in SEQ ID NO: 1 (MPLP-PHPGHP GYINFSYEVL TPLKWYQNMI RHPYTSY-GYE PMGGWLHHQI IPVVSQQTPQ SHA) (TRAP63), a homologue, analogue, or a pharmaceutically acceptable salt thereof, which can stimulate the tissue formation phase of a wound healing process, and a suitable pharmaceutical carrier and one or more enamel matrix polypeptides selected from the group of enamel matrix polypeptides which correspond to:

```
                                        SEQ ID NO: 2
a. (MPLPPHPGHPGYINFSYEVLTPLKWYQNMIRHP-

YTSYGYEPMG),

SEQ ID NO: 3
b. (MPLPPHPGHPGYINFSYEVLTPLKWYQNMIRHP-

YTSYGYEPMGGW),
   and

SEQ ID NO: 4
c. (MPLPPHPGHPGYINFSYEVLTPLKWYQNMIRHP-

SLLPDLPLEAWPATDKTKREEVD).
```

The small molecular weight enamel matrix polypeptide corresponding to the amino acid sequence shown in SEQ ID NO: 2 is in the present context referred to as TRAP43.

The small molecular weight enamel matrix polypeptide corresponding to the amino acid sequence shown in SEQ ID NO: 3 is in the present context referred to as TRAP45. The small molecular weight enamel matrix polypeptide corresponding to the amino acid sequence shown in SEQ ID NO: 4, which is identical to the amino acid sequence shown in Boabaid F., et al, J. Periodontol, Vol 75, No. 8, 2004, incorporated herein by reference, is in the present context referred to as LRAP56

Another pharmaceutical composition according to the present invention typically comprises an acid-extraction of enamel proteins and/or polypeptides derived from developing mammalian tooth buds, and is least 2×, such as 3×, 4×, 5×, 10×, 20×, or 100× enriched in an enamel matrix polypeptide, which is at least 80%, such as 90% identical to the amino acid sequence as shown in SEQ ID NO: 1 (TRAP63), a homologue, analogue, or a pharmaceutically acceptable salt thereof, which can stimulate the tissue formation phase of a wound healing process.

In one embodiment, a pharmaceutical composition comprising an enamel matrix polypeptide which is at least 80%, such as 90% identical to the amino acid sequence as shown in SEQ ID NO: 1 (TRAP63), a homologue, analogue, or a pharmaceutically acceptable salt thereof, which can stimulate the tissue formation phase of a wound healing process, consists of all isolated enamel polypeptides and/or proteins with a molecular weight (M.W.)<8 kDa, such as 7 kDa, derivable from a defined amount of developing mammal tooth buds, and a suitable pharmaceutical carrier.

Further, a process is disclosed for producing a pharmaceutical composition comprising an enamel matrix polypeptide which is at least 80%, such as 90% identical to the amino acid sequence as shown in SEQ ID NO: 1 (TRAP63), a homologue, analogue, or a pharmaceutically acceptable salt thereof, which can stimulate the tissue formation phase of a wound healing process, comprising:
 a. isolating the enamel proteins present in a defined amount of developing animal tooth buds, and
 b. removing any protein with a molecular weight (M.W.) 8 kDa from said isolate.

In said process, the enamel polypeptides can be isolated from human, porcine, bovine, rat, mouse and/or sheep developing tooth buds.

Consequently, a pharmaceutical composition comprising proteins with a molecular weight (M.W.)<8 kDa, such as ≤7 kDa is related to, wherein said composition is produced employing a process according to claim 6 or 7.

Alternatively, a pharmaceutical composition according to the present invention can comprise at least one enamel polypeptides which is produced by synthesis in vitro and/or in vivo, or which is a purified recombinant polypeptide fragment and/or which is synthetically and/or chemically altered.

A pharmaceutical composition according to the present invention can further comprise a pharmaceutically acceptable carrier which can be selected from the group consisting of PGA, PEG and/or EMD.

An enamel matrix polypeptide or a pharmaceutical composition according to the present invention can be used as a medicine such as for use in promoting wound healing, for use in treating an inflammatory condition and/or an infection, for use in promoting and/or improving periodontal soft tissue regeneration and/or stimulation of angiogenesis.

The present invention further for the first time discloses the use of an enamel matrix polypeptide or a pharmaceutical composition consisting of an enamel matrix polypeptide which is at least 80%, such as 90% identical to the amino acid sequence as shown in SEQ ID NO: 1 (TRAP63), a homologue, analogue, or a pharmaceutically acceptable salt thereof, which can stimulate the tissue formation phase of a wound healing process, and a suitable pharmaceutical carrier, which further can consist of one or more enamel matrix polypeptides selected from the group of enamel matrix polypeptides which correspond to:
a. SEQ ID NO: 2 (TRAP43),
b. SEQ ID NO: 3 (TRAP45), and
c. SEQ ID NO: 4 (LRAP56),
for the manufacture of a pharmaceutical composition for promoting wound healing, treating and/or preventing an inflammatory condition, treating and/or preventing an infection, promoting and/or improving periodontal soft tissue regeneration and/or stimulation of angiogenesis.

Also, a method is disclosed for promoting wound healing, treating and/or preventing an inflammatory condition, treating and/or preventing an infection, promoting and/or improving periodontal soft tissue regeneration and/or stimulation of angiogenesis, wherein a patient in need thereof is administered a pharmaceutical composition essentially consisting of an enamel matrix polypeptide or a pharmaceutical composition consisting of an enamel matrix polypeptide which is at least 80%, such as 90% identical to the amino acid sequence as shown in SEQ ID NO: 1 (TRAP63), a homologue, analogue, or a pharmaceutically acceptable salt thereof, which can stimulate the tissue formation phase of a wound healing process, and a suitable pharmaceutical carrier, which further can consist of one or more enamel matrix polypeptides selected from the group of enamel matrix polypeptides which correspond to:
a. SEQ ID NO: 2 (TRAP43),
b. SEQ ID NO: 3 (TRAP45), and
c. SEQ ID NO: 4 (LRAP56).

Wound Healing

Healing of periodontal tissue is a complex process, which involves formation of tissues and involves the interaction of several types of cells. Application of bioactive material is considered an important approach to improve the regeneration of periodontal tissue. Enamel matrix derivative (EMD) is a complex of low-molecular weight hydrophobic enamel proteins, which is derived from developing porcine tooth buds. The EMD-based commercial product Emdogain®, which contains also a propylene glycol alginate (PGA) carrier, has been used clinically since more than 10 years, and its capacity to promote periodontal regeneration has been largely documented. The influence of EMD on biological processes seems to be based to the presence of bioactive compounds, which mimic the process of teeth development.

The present invention is based on the finding that a pharmaceutical composition essentially consisting of an enamel matrix polypeptide or a pharmaceutical composition consisting of an enamel matrix polypeptide which is at least 80%, such as 90% identical to the amino acid sequence as shown in SEQ ID NO: 1 (TRAP63), a homologue, analogue, or a pharmaceutically acceptable salt thereof, and a suitable pharmaceutical carrier, which in one embodiment further can comprise of one or more enamel matrix polypeptides selected from the group of enamel matrix polypeptides which correspond to:
a. SEQ ID NO: 2 (TRAP43),
b. SEQ ID NO: 3 (TRAP45), and
c. SEQ ID NO: 4 (LRAP56),
is beneficial for the enhancement or improvement of the healing of wounds in collagen or epithelium containing tissues, including skin and mucosa. In particular, the herein for the first time described composition is found to be able to induce and/or promote the healing of tissue by stimulating the early tissue formation phase of the wound healing process. As demonstrated in the experimental section herein, the enamel matrix polypeptide which is at least 80%, such as 90% identical to the amino acid sequence as shown in SEQ ID NO: 1 (TRAP63) exerts especially useful effects in the healing or prophylaxis of soft tissue wounds.

Accordingly, the invention relates to the use of a preparation of an enamel matrix polypeptide which is at least 80%, such as 90% identical to the amino acid sequence as shown in SEQ ID NO: 1 (TRAP63) for the preparation of a pharmaceutical or cosmetical composition for stimulating the early tissue formation phase of a wound healing process and consequently for accelerating the onset of wound healing, for inducing and/or promoting the healing of tissue, for healing of a wound, for improving healing of a wound, and/or for soft tissue regeneration or repair.

As the presently described preparation and/or composition in particular induces the early tissue formation phase of a wound healing process, the preparation and/or composition is in one embodiment administered to a wound for rapid inducement and/or an accelerated onset of a wound healing and/or for inducing an over-all accelerated healing of a wound.

Furthermore, the enamel matrix polypeptide which is at least 80%, such as 90% identical to the amino acid sequence as shown in SEQ ID NO: 1 (TRAP63) has been found to have anti-bacterial and/or anti-inflammatory properties that can be used for treatment of both soft and hard tissue conditions.

Thus, the invention also relates to the use of a preparation of an enamel matrix polypeptide which is at least 80%, such as 90% identical to the amino acid sequence as shown in SEQ ID NO: 1 (TRAP63) for the preparation of a pharmaceutical composition for the prevention and/or treatment of infections or inflammatory conditions.

Wounds and/or ulcers are normally found on the skin or on mucosal surfaces. A wound may be a result of a soft tissue defect or a lesion or of an underlying condition. Regeneration of experimentally provoked periodontal wounds is also within the scope of the present invention. In the present context the term "skin" relates to the outermost surface of the body of an animal including a human and embraces intact or almost intact skin as well as injured skin surfaces. The term "mucosa" relates to undamaged or damaged mucosa of an animal such as a human and may be the oral, buccal, aural, nasal, lung, eye, gastrointestinal, vaginal, or rectal mucosa.

In the present context the term "wound" denotes a bodily injury with disruption of the normal integrity of tissue structures. The term is also intended to encompass the terms "sore", "lesion" and "ulcer". Normally, the term "sore" is a popular term for almost any lesion of the skin or mucous membranes and the term "ulcer" is a local defect, or excavation, of the surface of an organ or tissue, which is produced by the sloughing of necrotic tissue. Lesion generally relates to any tissue defect.

The term "wound" used in the present context denotes any wound (see below for a classification of wounds) and at any particular stage in the healing process including the stage before any healing has initiated.

Examples of wounds which can be prevented and/or treated in accordance with the present invention are, e.g., aseptic wounds, contused wounds, incised wounds, lacerated wounds, non-penetrating wounds (i.e. wounds in which there is no disruption of the skin but there is injury to underlying structures), open wounds, penetrating wounds, perforating wounds, puncture wounds, septic wounds, subcutaneous wounds, etc. Examples of sores are bed sores, cankers sores, chrome sores, cold sores, pressure sores etc. Examples of ulcers are, e.g., peptic ulcer, duodenal ulcer, gastric ulcer, gouty ulcer, diabetic ulcer, hypertensive ischemic ulcer, stasis ulcer, sublingual ulcer, submucous ulcer, symptomatic ulcer, trophic ulcer, tropical ulcer, veneral ulcer, etc. However, there is often a certain overlap between the use of the terms "wound" and "ulcer" and "wound" and "sore" and, furthermore, the terms are often used at random. Therefore as mentioned above, in the present context the term "wound" encompasses the term "ulcer", "lesion" and the term "sore" and the terms are indiscriminately used unless otherwise indicated.

The kinds of wounds to be treated according to the invention include also i) general wounds such as, e.g., surgical, traumatic, infectious, ischemic, thermal, chemical and bullous wounds; ii) wounds specific for the oral cavity such as, e.g., post-extraction wounds, endodontic wounds especially in connection with treatment of cysts and abscesses, ulcers and lesions of bacterial, viral or autoimmunological origin, mechanical, chemical, thermal, infectious and lichenoid wounds; herpes ulcers, stomatitis aftosa, acute necrotising ulcerative gingivitis and burning mouth syndrome are specific examples; and iii) wounds on the skin such as, e.g., neoplasm, burns (e.g. chemical, thermal), lesions (bacterial, viral, autoimmunological), bites and surgical incisions. Another way of classifying wounds is as i) small tissue loss due to surgical incisions, minor abrasions and minor bites, or as ii) significant tissue loss. The latter group includes ischemic ulcers, pressure sores, fistulae, lacerations, severe bites, thermal burns and donor site wounds (in soft and hard tissues).

The healing effect of an enamel matrix polypeptide which is at least 80%, such as 90% identical to the amino acid sequence as shown in SEQ ID NO: 1 (TRAP63) has been found to be of interest in connection with wounds which are present in the oral cavity. Such wounds may be bodily injuries or trauma associated with oral surgery including periodontal surgery, tooth extraction(s), endodontic treatment, insertion of tooth implants, application and use of tooth prothesis, and the like. In the experimental section herein the beneficial effect of an enamel matrix polypeptide which is at least 80%, such as 90% identical to the amino acid sequence as shown in SEQ ID NO: 1 (TRAP63) on such wounds has been demonstrated. Furthermore, a soft tissue healing effect has been observed.

In the oral cavity, healing of wounds like aphthous wounds, traumatic wounds or herpes associated wounds is also improved after application of an enamel matrix polypeptide which is at least 80%, such as 90% identical to the amino acid sequence as shown in SEQ ID NO: 1 (TRAP63) or a composition as described herein. The traumatic wounds and the herpes associated wounds can of course also be situated on other parts of the body than in the oral cavity.

In other aspects of the invention, the wound to be prevented and/or treated is selected from the group consisting of aseptic wounds, contused wounds, incised wounds, lacerated wounds, non-penetrating wounds, open wounds, penetrating wounds, perforating wounds, puncture wounds, septic wounds and subcutaneous wounds.

Other wounds which are of importance in connection with the present invention are wounds like ischemic ulcers, pressure sores, fistulae, severe bites, thermal burns and donor site wounds.

Ischemic ulcers and pressure sores are wounds, which normally only heal very slowly and especially in such cases an improved and more rapid healing is of course of great importance for the patient. Furthermore, the costs involved in the treatment of patients suffering from such wounds are markedly reduced when the healing is improved and takes place more rapidly.

Donor site wounds are wounds which e.g. occur in connection with removal of hard tissue from one part of the body to another part of the body e.g. in connection with transplantation. The wounds resulting from such operations are very painful and an improved healing is therefore most valuable.

The term "skin" is used in a very broad sense embracing the epidermal layer of the skin and—in those cases where the skin surface is more or less injured—also the dermal layer of the skin. Apart from the stratum corneum, the epidermal layer of the skin is the outer (epithelial) layer and the deeper connective tissue layer of the skin is called the dermis.

Since the skin is the most exposed part of the body, it is particularly susceptible to various kinds of injuries such as, e.g., ruptures, cuts, abrasions, burns and frostbites or injuries arising from various diseases. Furthermore, much skin is often destroyed in accidents. However, due to the important barrier and physiologic function of the skin, the integrity of the skin is important to the well-being of the individual, and any breach or rupture represents a threat that must be met by the body in order to protect its continued existence.

Apart from injuries on the skin, injuries may also be present in all kinds of tissues (i.e. soft and hard tissues). Injuries on soft tissues including mucosal membranes and/or skin are especially relevant in connection with the present invention.

Healing of a wound on the skin or on a mucosal membrane undergoes a series of stages that results either in repair or regeneration of the skin or mucosal membrane. In recent years, regeneration and repair have been distinguished as the two types of healing that may occur. Regeneration may be defined as a biological process by which the architecture and function of lost tissue are completely renewed. Repair, on the other hand, is a biological process by which continuity of disrupted tissue is restored by new tissues which do not replicate the structure and function of the lost ones.

The majority of wounds heal through repair, meaning that the new tissue formed is structurally and chemically unlike the original tissue (scar tissue). In the early stage of the tissue repair, one process is almost always involved and that is the formation of a transient connective tissue in the area of tissue injury. This process starts by forming a new extracellular collagen matrix by fibroblast. This new extracellular collagen matrix is then the support for a connective tissue during the final healing process. The final healing is in most tissues a scar formation containing connective tissue. In tissues which have regenerative properties, such as, e.g., skin and bone, the final healing includes regeneration of the original tissue. This regenerated tissue has frequently also some scar characteristics, e.g. a thickening of a healed bone fracture.

Under normal circumstances, the body provides mechanisms for healing injured skin or mucosa in order to restore the integrity of the skin barrier or the mucosa. The repair process for even minor ruptures or wounds may take a period of time extending from hours and days to weeks. However, in ulceration, the healing may persist for an extended period of time, i.e. months or even years.

The stages of wound healing normally include inflammation (normally 1-3 days), migration (normally 1-6 days), proliferation (normally 3-24 days) and maturation (normally 1-12 months). The healing process is a complex and well-orchestrated physiological process that involves migration, proliferation and differentiation of a variety of cell types as well as synthesis of matrix components. The healing process may be separated into the following three phases: i) Haemostasis and inflammation, ii) Granulation tissue formation and re-epithelization, iii) Dermal remodeling.

All of the above-mentioned healing processes take considerable time. The rate of healing is influenced by the wound's freedom from infection, the general health of the individual, presence of foreign bodies, etc. Some pathologic conditions like infection, maceration, drying out, generally poor health and malnutrition can lead to formation of a chronic ulcer Until at least superficial healing has occurred, the wound remains at risk of continued or new infection. Therefore, the quicker the wound can heal, the sooner the risk is removed Thus, any procedure that can influence the rate of wound healing or favorably influence the healing of wounds, and in particular, any procedure or use of composition, such as the preparation and/or composition described herein, which can accelerate the onset of the wound healing process, is of great value.

Furthermore, as almost all tissue repair processes include the early connective tissue formation, a stimulation of this and the subsequent processes are contemplated to be of uttermost influence to improve tissue healing.

In the present context the term "clinical healing" is used to denote a situation where no tissue interruption can be visually observed and only discrete signs of inflammation are present such as a light redness or a discretely swollen tissue. In addition, no complaints of pain are present when the organ is relaxed or untouched.

As mentioned above, the invention relates to the use enamel matrix polypeptide which is at least 80%, such as 90% identical to the amino acid sequence as shown in SEQ ID NO: 1 (TRAP63) as a wound healing agent, i.e. an agent which accelerates, stimulates or promotes healing of dermal or mucosal wounds. Accordingly, an important use is also the use as tissue regeneration and/or repair agents.

Traditionally, dry or wet-to-dry dressings have been most commonly used for wound care. These are step by step being replaced by moist environments using occlusive dressings. To successfully repair or replace a failed body part, the processes of wound healing, fibrosis and microbial invasion must be balanced against each other. Many tools available to ward off infection compromise wound healing. Delayed wound healing or inflammation can exacerbate fibrosis. Moreover, it has previously been suggested that growth factors like epidermal growth factor (EGF), transforming growth factor-α (TGF-α), platelet derived growth factor (PDGF), fibroblast growth factors (FGFs) including acidic fibroblast growth factor (α-FGF) and basic fibroblast growth factor (6-FGF), transforming growth factor-j3 (TGF-β) and insulin like growth factors (IGF-1 and IGF-2) are conductors of the wound healing process and they are frequently cited as promoters of wound healing; however, they can actually drive fibrosis which in turn can itself impair successful healing. Even though accelerated healing offers the most promise for reducing the risk of infection and the resulting inflammation that can drive scar formation, therapeutic attempts to accelerate the normal wound healing process have met with relatively little success. This is likely because the repair process involves the concerted involvement of a number of factors, cf. above.

In the oral cavity the use of dressings is common. Such dressings are of the traditional type, e.g. Surgipads to stop bleeding and Coe-Pack periodontal dressing (Coe Laboratories, the GC Group, Chigago, USA) on open wounds, Gaze drenched in antibiotic solution is inserted in tooth extraction alveoli and requires removal after a few days when the healing has started. Rinsing with antiseptics such as chlorhexidine is regularly used after oral surgery. Sometimes general or topical antibiotics are also prescribed.

In general specific precautions have to be taken into considerations in connection with treatment of wounds, such as, e.g., sterility considerations, contamination problems, correct application of bandages/dressings etc. which normally require that the treatment/application is performed by well-educated nurses or the like. Thus, wound treatment often becomes a very expensive operation when the wound healing agent is to be applied several times daily. A desired reduction in the costs involved in wound healing treatment is therefore obtainable when the application frequency can be reduced or if the healing processes are improved leading to a reduction in the time period required to heal the wound.

EMD and Woundhealing

Angiogenesis is an important process involved in the periodontal regeneration and wound healing. Periodontium is highly vascularised tissue and therefore success of therapy depends on the ability to promote the formation of blood microvessels, which guarantee nutrition and oxygen supply. Endothelial cells (ECs, which underlie the inner surface of the vasculature, play a key role in the angiogenesis. The process of new vessel formation includes sprouting of ECs from the existing vessel, proliferation, migration, and organization in the capillary network. An ability of EMD to stimulate angiogenesis in vivo was shown by both clinical and animal studies. The angiogenic activity of EMD was also investigated in in vitro studies using endothelial cells. There are contradictory data on the effect of EMD on endothelial cell proliferation: some studies found no proliferative effect of EMD on ECs, whereas other studies found that ECs proliferation is stimulated by EMD. Most studies indicate that EMD possess chemotactic ability and stimulate ECs migration. The presently disclosed study on human umbilical vein endothelial cells (HUVECs) shows that EMD increase the expression of several genes involved in angiogenesis, namely angiopoetin-2, E-selectin, and intercellular adhesion molecule 1 (ICAM-1).

In the present study, the contribution of different EMD proteins to its general angiogenic activity was investigated. Two fractions of proteins were separated from EMD: the first fraction included proteins with a molecular weight of 8-55 kDa; the second fraction included proteins with a molecular weight less than 8 kDa. The effect of these fractions on the viability and differentiation of HUVECs was analysed in vitro. The expression of several proteins involved in wound healing and angiogenesis was examined: ang-2, E-selectin, ICAM-1, von Willebrand factor (vWF), vascular endothelial growth factor (VEGF) receptor-1 (Flt-1), and VEGF receptor-2 (KDR).

As is documented in the experimental part of the present application, two EMD fractions were separated by size exclusion chromatography and their effect on the viability and differentiation of human umbilical vein endothelial cells in vitro was investigated. Fraction LMW-depleted comprised the proteins with a molecular weight of 8 to approximately 55 kDa. The major component of this fraction is the 20 kDa amelogenin. Fraction LMW contained mainly enzymatically degraded amelogenin peptides with a molecular weight <8 kDa. The viability and gene expression levels of several proteins involved in wound healing and angiogenesis were investigated using the MTT assay and real-time PCR, respectively.

The viability of HUVECs was significantly decreased after treatment with fractions LMW-depleted and LMW and slightly increased by EMD at 100 µg/ml. The reasons for the different effect of EMD and EMD fractions on cell viability are not entirely clear. Some components of EMD might induce a decrease in viability of HUVECs, and the amount of these proteins is proportionally higher in the fractions than in the original EMD.

Both fractions LMW-depleted and LMW induced the expression of adhesion molecules E-selectin and ICAM-1 in HUVECs. However, the effect of LMW-depleted on the expression of adhesion molecules was higher than that of LMW and comparable to that of EMD. E-selectin and ICAM-1 mediate the adhesion of inflammatory cells to the endothelium and their migration to wound sites. Increased expression of adhesion molecules in wound areas will attract inflammatory cells, which is an important factor of angiogenesis. Amelogenin is the main component of fraction LMW-depleted and presents itself as the most promising candidate for inducing the adhesion molecule expression in HUVECs. This hypothesis is supported by a mice study, which showed that amelogenin gene splice products induce recruitment of inflammatory cells into pulp. The mechanisms by which EMD and/or amelogenin affect adhesion molecule expression are currently under investigation. A possible mechanism might involve activation of ERK-1/2, which is known to control the expression of E-selectin and ICAM-1. A recent in vitro study on odontoblasts showed that amelogenin induced activation of ERK-1/2 kinase, but the significance of this pathway in endothelial cells needs to be verified.

The increase of VEGF receptor Flt-1 and KDR gene expression by treatment of HUVECs with EMD was showed for the first time in the present study. VEGF is a crucial regulator of angiogenesis and increased expression of VEGF receptors in endothelial cells leads to activation of angiogenesis. It may therefore be reasoned that EMD-induced increase of VEGF receptor gene expression may play an important role in the regeneration of the periodontium. Some previous in vitro studies showed that EMD induced the production of VEGF by cells of the periodontium, particularly human gingival fibroblasts and periodontal ligament cells. Enhanced production of VEGF by cells of the periodontium in response to EMD on the one hand, and the increase in the expression of VEGF receptors in endothelial cells on the other hand might be important mechanisms underlying the ability of EMD proteins to induce angiogenesis and periodontal healing in vivo. These proposed mechanisms of EMD effects in vivo are supported by a recent clinical study in which the application of Emdogain onto the root surface and into the periodontal pocket resulted in the increase of VEGF expression and microvessel density in gingival tissues. The present data suggest that EMD low molecular weight protein are responsible for the up-regulation of VEGF receptor expression, because it was affected mainly by LMW but not by LMW-depleted. EMD induced a significant increase in the expression of ang-2. A similar tendency was also observed for LMW-depleted, although this effect was not statistically significant. In contrast, no effect of LMW on the expression of ang-2 was observed. Ang-2 is one of the crucial proteins involved in angiogenesis: it is implicated in vessel maturation and facilitates endothelial cell responsiveness to angiogenic and inflammatory stimuli. Thus, it seems that EMD proteins with different molecular weights affect the ang-2 expression differently.

It was further found that the expression of vWF is up-regulated by EMD and LMW. In contrast, no significant effect of LMW-depleted on vWF expression was observed. WF is involved in the platelet adhesion, and platelet, in turn, might release several factors supporting angiogenesis and wound healing. The present results suggest that low molecular weight EMD proteins are involved in inducing vWF gene expression in endothelial cells. Interestingly, vWF production in endothelial cells is controlled by KDR. It stands to reason that the increase of vWF expression is directly linked to the up-regulation of KDR expression by LMW.

Wound healing is a complicated process which consists of different phases that overlap in time: hemostasis, inflammation, tissue formation, and tissue remodelling. Angiogenesis plays an important role in all phases of wound healing: hemostatic clot formation provides a provisional matrix for tissue formation; blood vessels supply nutrients and oxygen and facilitate access of inflammatory cells to the wound. The present data suggest that EMD proteins of different molecular weights cover various aspects of angiogenesis. Particularly, proteins with a molecular weight >8 kDa seem to stimulate the inflammatory phase of wound healing, which is implied by the strong up-regulation of adhesion molecules E-selectin and ICAM-1 by LWM-depleted. EMD proteins with a molecular weight <8 kDa stimulate the expression of VEGF receptors and vWF. It is probable that the presence of proteins from both LMW and LMW-depleted is important for the observed angiogenic activity of EMD. This hypothesis is supported by a recent study on mice, in which the effect of EMD-derived protein pools with different molecular weights on blood vessel formation was investigated in vivo.

The authors determined the highest angiogenic activity for EMD protein pools containing proteins with a molecular weight of 25, 7, and 5 kDa.

In summary, the presently presented data clearly demonstrates that EMD proteins with different molecular weights possess different biological activities.

TRAP 63

Amelogenin splice variants and proteolytic cleavage products are the main compounds isolated from EMD.

During cementogenesis in the developing tooth, amelogenin, as described above, due to alternative splicing of the primary transcript and the following proteolytic processing of the secreted proteins, degrades into smaller pieces (fragments and polypeptide fragments), and these pieces are hypothesised to interact differentially with the surrounding tissue and promote serial steps in the development of the periodontal system.

The present invention is based on the identification and isolation of a specific low molecular weight fraction of porcine EMD, separated by High Pressure Liquid Chromatography (HPLC), hereafter termed fraction LMW, which is for the first time shown to comprise a novel small molecular weight enamel matrix polypeptide, which is at least 80%, such as 90% identical to the amino acid sequence as shown in SEQ ID NO: 1 (MPLPPHPGHP GYINFSYEVL TPLKWYQNMI RHPYTSYGYE PMGGWLHHQI IPWSQQTPQ SHA), a homologue, analogue, or a pharmaceutically acceptable salt thereof. The novel small molecular weight enamel matrix polypeptide corresponding to the amino acid sequence shown in SEQ ID NO: 1 is in the present context referred to as TRAP63.

The present invention further discloses a specific low molecular weight fraction of porcine EMD, separated by High Pressure Liquid Chromatography (HPLC), hereafter termed fraction LMW, which consists of an enamel matrix polypeptide which is at least 80%, such as 90% identical to the amino acid sequence as shown in SEQ ID NO: 1 (MPLPPHPGHP GYINFSYEVL TPLKWYQNMI RHPYTSYGYE PMGGWLHHQI IPWSQQTPQ SHA) (TRAP63), a homologue, analogue, or a pharmaceutically acceptable salt thereof, and the enamel matrix polypeptides selected from the group of enamel matrix polypeptides which correspond to:

```
                                            SEQ ID NO: 2
a.  (MPLPPHPGHPGYINFSYEVLTPLKWYQNMIRHP-

YTSYGYEPMG) ,

SEQ ID NO: 3
b.  (MPLPPHPGHPGYINFSYEVLTPLKWYQNMIRHP-

YTSYGYEPMGGW) ,
    and

SEQ ID NO: 4
c.  (MPLPPHPGHPGYINFSYEVLTPLKWYQNMIRHP-

SLLPDLPLEAWPATDKTKREEVD) .
```

The small molecular weight enamel matrix polypeptide corresponding to the amino acid sequence shown in SEQ ID NO: 2 is in the present context referred to as TRAP43. The small molecular weight enamel matrix polypeptide corresponding to the amino acid sequence shown in SEQ ID NO: 3 is in the present context referred to as TRAP45. The small molecular weight enamel matrix polypeptide corresponding to the amino acid sequence shown in SEQ ID NO: 4 is in the present context referred to as LRAP56.

Said specific low molecular weight fraction of porcine EMD, separated by High Pressure Liquid Chromatography (HPLC), hereafter termed fraction LMW, as well as the isolated polypeptides in varying combinations with each other, execute specific biological functions that are closely related to, but not identical to the effects prior observed with EMD, or full-length amelogenin.

The term "periodontal cells", in the present context, refers to cells such as periodontal ligament cells (PDL), gingival cells, epithelial cells and/or bone cells, but is not limited thereto.

"Differentiation" of a cell, refers to a process by which a cell undergoes a change to an overtly specialized cell type. Such a cell may be a stem cell differentiating into other specialized cell types during embryogenesis or later stages of development, or any other cell receiving instructions to do so.

"Proliferation" of a cell refers to a stage wherein the cell actively is growing and dividing to generate a cell population of a greater size. Such proliferation may be stimulated by external stimuli, such as growth factors etc.

"Mesenchyme" refers to an immature, unspecialized form of connective tissue in animals, consisting of cells embedded in a tenuous extracellular matrix. Embryonic connective tissue derivable from mesoderm, is named mesenchyme. "Mesenchymal stem cells" are undifferentiated mesenchyme cells, such as bone marrow cells. In a presently preferred embodiment, said mesenchymal stem cells are differentiated into e.g. osteoblasts, osteoclasts, or any other bone cell.

The present invention for the first time discloses the use of an enamel matrix polypeptide which is at least 80%, such as 90% identical to the amino acid sequence as shown in SEQ ID NO: 1 (TRAP63), a homologue, analogue, or a pharmaceutically acceptable salt thereof, which can stimulate the tissue formation phase of a wound healing process, or a pharmaceutical composition consisting of an enamel matrix polypeptide which is at least 80%, such as 90% identical to the amino acid sequence as shown in SEQ ID NO: 1 (TRAP63), a homologue, analogue, or a pharmaceutically acceptable salt thereof, which can stimulate the tissue formation phase of a wound healing process, and a suitable pharmaceutical carrier, which further can consist of one or more enamel matrix polypeptides selected from the group of enamel matrix polypeptides which correspond to a. SEQ ID NO: 2 (TRAP43),
b. SEQ ID NO: 3 (TRAP45), and
c. SEQ ID NO: 4 (LRAP56), for the manufacture of a pharmaceutical composition for promoting accelerated onset of wound healing, treating and/or preventing an inflammatory condition, treating and/or preventing an infection, promoting and/or improving periodontal soft tissue regeneration and/or stimulation of angiogenesis.

The present invention relates to the use of the isolated LMW fraction and/or the use of an enamel matrix polypeptide which is at least 80%, such as 90% identical to the amino acid sequence as shown in SEQ ID NO: 1 (TRAP63), a homologue, analogue, or a pharmaceutically acceptable salt thereof, which can stimulate the tissue formation phase of a wound healing process, for application on medical implants or devices.

The invention also relates to medical implants or devices onto which the isolated LMW fraction and/or the use of an enamel matrix polypeptide which is at least 80%, such as 90% identical to the amino acid sequence as shown in SEQ ID NO: 1 (TRAP63), a homologue, analogue, or a pharmaceutically acceptable salt thereof, which can stimulate the tissue formation phase of a wound healing process, has been applied.

According to the present invention, the implant or device may be any implant or device intended for use in the human or animal body, in particular in the dental area, gastrointestinal tract, urethra, bladder, pulmonary cavity, lungs, trachea, larynx, oesophagus, joints, bone, skull, ears, sinuses, veins, arteries or abdominal cavity. The implant can a bone substitute material, such as ceramic and or plaster.

The implant or device may be used for fixation of complicated fractures, e.g. of the neck, legs or arms, or skull fractures, thus the implant or device may be a pin or screw or bone substitute material, conventionally used to immobilise (fix) fragments of fractured bone. Such pins or screws typically comprise a portion that penetrates the skin of the patient at or near the site of the fracture. Pins and screws for this purpose may conventionally be prepared from a metal such as titanium or steel, and may optionally be coated with a polymeric material which may typically be biodegradable or stabilised to facilitate soft tissue closure and sealing. Furthermore, an implant may be an electrical conductor such as one used in, e.g., pacemakers, brain implants or biosensors. The implant may also be an artificial tooth or a dental prothesis, such as a screw and/or an abutment.

Before application on an implant or device, the isolated LMW fraction and/or the enamel matrix polypeptide which is at least 80%, such as 90% identical to the amino acid sequence as shown in SEQ ID NO: 1 (TRAP63), a homologue, analogue, or a pharmaceutically acceptable salt thereof, which can stimulate the tissue formation phase of a wound healing process, may be admixed with other ingredients, e.g. pharmaceutically acceptable excipients to constitute a pharmaceutical composition, as discussed below, and coated onto the surface of the implant or device, e.g. by dipping the relevant portion of the implant or device in a solution or dispersion of the active enamel substance or by spraying a solution or dispersion of the active enamel substance onto the relevant surface of the implant or device followed, in both cases, by drying. On application, the isolated LMW fraction and/or the enamel matrix polypeptide which is at least 80%, such as 90% identical to the amino acid sequence as shown in SEQ ID NO: 1 (TRAP63), a homologue, analogue, or a pharmaceutically acceptable salt thereof, which can stimulate the tissue formation phase of a wound healing process, is adsorbed to the surface of the implant or device and may be fixed thereon by means of conventional fixatives such as formaldehyde, glutaraldehyde or ethanol. Alternatively, the isolated LMW fraction and/or the enamel matrix polypeptide which is at least 80%, such as 90% identical to the amino acid sequence as shown in SEQ ID NO: 1 (TRAP63), a homologue, analogue, or a pharmaceutically acceptable salt thereof, which can stimulate the tissue formation phase of a wound healing process, may be applied on the relevant surface of the implant or device by cross-linking said fraction and/or polypeptide fragment of an active enamel substance, to a polymer component of the implant or device, e.g. by UV radiation or chemical treatment in a manner known per se, or by covalently binding the fraction and/or polypeptide fragment to a suitable functional group of a polymeric component present on the surface of the implant or device.

The amount of the isolated LMW fraction and/or the enamel matrix polypeptide which is at least 80%, such as 90% identical to the amino acid sequence as shown in SEQ ID NO: 1 (TRAP63), a homologue, analogue, or a pharmaceutically acceptable salt thereof, which can stimulate the tissue formation phase of a wound healing process, applied on the appropriate surface of the implant or device will normally result in an amount of total protein per $cm^2$ area of the implant or device corresponding to from about 0,005 $mg/cm^2$ to about 20 $mg/cm^2$ such as from about 0.01 $mg/cm^2$ to about 15 $mg/cm^2$.

In accordance with the present invention, application of the isolated LMW fraction and/or the enamel matrix polypeptide which is at least 80%, such as 90% identical to the amino acid sequence as shown in SEQ ID NO: 1 (TRAP63), a homologue, analogue, or a pharmaceutically acceptable salt thereof according to the present invention on a surface of an implant or device for the present purpose may optionally be combined with application of other types of suitable biologically active substances, e.g. antimicrobial agents such as antibacterial or antifungal agents, or application of bacteriostatic agents or disinfectants for the prevention or treatment of microbial infections at the site where the implant or device is in contact with epithelial tissue.

"Soft tissues", (i.e. non-mineralised tissues), can in the present context be used interchangeably with gingival tissue, and may be defined as collagen or epithelium containing tissues, including skin and mucosa, muscle, blood and lymph vessels, nerve tissues, glands, tendons, eyes and cartilage. In general the fraction and/or polypeptide fragments of the present invention can be used to promote healing or for manufacturing a pharmaceutical composition for promoting healing of a wound not only in skin and mucosa, but in any gingival tissue of the patient in need thereof.

The term "hard-tissue formation" in "mineralised tissue" may be summarised as the production by cells of an organic matrix capable of accepting mineral, with the activity of the enzyme alkaline phosphatase and a good blood supply prerequisites.

In accordance with the present invention, the isolated LMW fraction and/or the enamel matrix polypeptide which is at least 80%, such as 90% identical to the amino acid sequence as shown in SEQ ID NO: 1 (TRAP63), a homologue, analogue, or a pharmaceutically acceptable salt thereof is produced naturally by alternate splicing or processing, or by either enzymatic or chemical cleavage of a natural length protein, or by synthesis of polypeptides in vitro or in vivo (e.g. recombinant DNA methods and/or cultivation of diploid cells) will typically originate from porcine.

None withstanding, in light of the well-known fact that amelogenin is an evolutionary conservative protein, and the homology in between the species is documented to be high, it is presently envisioned or that analogous sequences might be found in rat, human, or mouse enamel matrix proteins, e.g. in amelogenin, which exert similar biological effects, e.g. possess osteogenic activity. The present invention consequently also encompasses analogue sequences to porcine amelogenin fragments as disclosed in ID.SEQ.NO.: 1 which are at least 80-95% identical to at least one of the amino acid sequences shown in ID.SEQ.NO: 1 and 2, such as at least 80%, 81%, 82%, 83%, 84%, 85%, 86%, 87%, 88%, 89%, 90%, 91%, 92%, 93%, 94%, 95%, 96%, 97%, 98%, 99%, or 99.5% identical, and which show analogue biological activity, i.e. which can stimulate the tissue formation phase of a wound healing process. In the present invention, such analogue polypeptides are envisioned to be usable for producing medicaments and/or pharmaceutical and/or cosmetical compositions for inducing soft tissue wound healing and/or for promoting angiogenesis and/or for supressing an inflammatory condition.

In the present invention, a polypeptide fragment selected from the group consisting the isolated LMW fraction and/or the enamel matrix polypeptide which is at least 80%, such as 90% identical to the amino acid sequence as shown in SEQ ID NO: 1 (TRAP63), a homologue, analogue, or a pharmaceutically acceptable salt thereof, which can stimulate the tissue formation phase of a wound healing process, can be selected from a polypeptide fragment isolated from mammalian tissue, a purified recombinant polypeptide fragment, or a polypeptide fragment which is synthetically manufactured. As is well known in the art, a recombinantly produced polypeptide will differ slightly from the endogenous template protein, especially when it is produced in a prokaryotic system. The present invention encloses recombinantly produced polypeptide fragments which are at least 95% identical to at least one of the amino acid sequences shown in ID.SEQ.NO: 1 and 2, such 93%, 94%, 95%, 96%, 97%, 98%, 99%, or 99.5% identical, and which show analogue biological activity, i.e. which can stimulate the tissue formation phase of a wound healing process.

A synthetically manufactured polypeptide on the other hand, as is well known in the art, can of course be designed to carry a diversity of chemical permutations that will not hinder and/or effect its original biological activity, e.g. its anti-inflammatory, or its pro-angiogenetic activity. Consequently, the present invention encloses also synthetically permutated polypeptide fragments which are at least 80-95% identical to enamel matrix polypeptide which is at least 80%, such as 90% identical to the amino acid sequence as shown in SEQ ID NO: 1 (TRAP63), a homologue, analogue, or a pharmaceutically acceptable salt thereof, such as at least 80%, 81%, 82%, 83%, 84%, 85%, 86%, 87%, 88%, 89%, 90%, 91%, 92%, 93%, 94%, 95%, 96%, 97%, 98%, 99%, or 99.5% identical, and which show analogue biological activity, i.e. which can stimulate the tissue formation phase of a wound healing process.

Additionally, any conservative variant of the sequence of a polypeptide fragment which is at least 80-95% identical to enamel matrix polypeptide which is at least 80%, such as 90% identical to the amino acid sequence as shown in SEQ ID NO: 1 (TRAP63), a homologue, analogue, or a pharmaceutically acceptable salt thereof, such as at least such as at least 80%, 81%, 82%, 83%, 84%, 85%, 86%, 87%, 88%, 89%, 90%, 91%, 92%, 93%, 94%, 95%, 96%, 97%, 98%, 99%, or 99.5% identical, and which shows analogue biological activity, i.e. which can stimulate the tissue formation phase of a wound healing process, is by virtue of its functional relationship to said sequences considered to be inside the scope of the present invention.

A conservative variant of a sequence is in the present context defined as an amino acid sequence which is conserved at least such as at least 80%, 81%, 82%, 83%, 84%, 85%, 86%, 87%, 88%, 89%, 90%, 91%, 92%, 93%, 94%, 95%, 96%, 97%, 98%, 99%, or 99.5%, when comparing variants of the same amino acid sequence between different species. The degree of conservation of a variant can, as is well known in the field, be calculated according to its derivation of PAM (see Dayhoff, Schwartz, and Orcutt (1978) Atlas Protein Seq. Struc. 5:345-352), or based on comparisons of Blocks of sequences derived from the Blocks database as described by Henikoff and Henikoff (1992) Proc Natl Acad Sci USA 89(22):10915-9.

Conservative substitutions may be made, for example according to table 1 below. Amino acids in the same block in the second column and preferably in the same line in the third column may be substituted for each other:

TABLE 1

| ALIPHATIC | Non-polar | G A P |
| | | I L V |
| | Polar - uncharged | C S T M |
| | | N Q |

TABLE 1-continued

| | Polar - charged | D E |
| | | K R |
| AROMATIC | | H F W Y |

Such replacements may also be made by unnatural amino acids include; alpha* and alpha-disubstituted* amino acids, N-alkyl amino acids*, lactic acid*, halide derivatives of natural amino acids such as trifluorotyrosine*, p-Cl-phenylalanine*, p-Br-phenylalanine*, p-I-phenylalanine*, L-allylglycine*, β-alanine*, L-a-amino butyric acid*, L-g-amino butyric acid*, L-a-amino isobutyric acid*, L-e-amino caproic acid #, 7-amino heptanoic acid*, L-methionine sulfone #*, L-norleucine*, L-norvaline*, p-nitro-L-phenylalanine*, L-hydroxyproline #, L-thioproline*, methyl derivatives of phenylalanine (Phe) such as 4-methyl-Phe*, pentamethyl-Phe*, L-Phe (4-amino)#, L-Tyr (methyl)*, L-Phe (4-isopropyl)*, L-Tic (1,2,3,4-tetrahydroisoquinoline-3-carboxyl acid)*, L-diaminopropionic acid # and L-Phe (4-benzyl)*. The notation * is herein utilised to indicate the hydrophobic nature of the derivative whereas # is utilised to indicate the hydrophilic nature of the derivative, #* indicates amphipathic characteristics.

Variant amino acid sequences may include suitable spacer groups that may be inserted between any two amino acid residues of the sequence including alkyl groups such as methyl, ethyl or propyl groups in addition to amino acid spacers such as glycine or b-alanine residues. A further form of variation, involves the presence of one or more amino acid residues in peptoid form, which will be well understood by those skilled in the art. For the avoidance of doubt, "the peptoid form" is used to refer to variant amino acid residues wherein the a-carbon substituent group is on the residue's nitrogen atom rather than the α-carbon. Processes for preparing peptides in the peptoid form are known in the art, see for example, Simon R J et al., PNAS (1992) 89(20), 9367-9371 and Norwell D C, Trends Biotechnol. (1995) 13(4), 132-134.

Polypeptides of the invention may be in a substantially isolated form. It will be understood that it may be mixed with carriers or diluents, which will not interfere with the intended purpose of the polypeptide and still be regarded as substantially isolated. A polypeptide of the invention may also be in a substantially purified form, in which case it will generally comprise the polypeptide or a fragment thereof in a preparation in which more than 90%, e.g. 95%, 98% or 99% of the protein in the preparation is a polypeptide of the invention.

EMD is processed as described in the experimental section

Active Enamel Substances

As used herein, "enamel matrix" means a precursor to enamel and may be obtained from any relevant natural source, i.e. a mammal in which teeth are under development. A suitable source is developing teeth from slaughtered animals such as, e.g., calves, pigs or lambs. Another source is e.g. fish skin. In the present context, the term "an active enamel substance" is used to encompass enamel matrix derivatives and/or enamel matrix proteins non-discriminant of their source.

Enamel matrix can be prepared from developing teeth as described previously (EP-B-0 337 967 and EP-B-0 263 086). The enamel matrix is scraped off and enamel matrix derivatives are prepared, e.g. by extraction with aqueous solution such as a buffer, a dilute acid or base or a water/solvent mixture, followed by size exclusion, desalting or other purification steps, alternatively followed by freeze-drying. Enzymes may alternatively be deactivated by treatment with heat or solvents, in which case the derivatives may be stored in liquid form without freeze-drying.

As an alternative source of the enamel matrix derivatives or proteins one may also use generally applicable synthetic routes, well known to a person skilled in the art, or use cultivated eukaryotic and/or prokaryotic cells modified by DNA-techniques. The enamel matrix proteins may thus be of recombinant origin and alternatively genetically and/or chemically modified (see, e.g., Sambrook, J. et al.: Molecular Cloning, Cold Spring Harbor Laboratory Press, 1989).

In the present context, enamel matrix derivatives are derivatives of enamel matrix which include one or several enamel matrix proteins or parts or fragments of such proteins, produced naturally by alternate splicing or processing, or by either enzymatic or chemical cleavage of a natural length protein, or by synthesis of polypeptides in vitro or in vivo (e.g. recombinant DNA methods and/or cultivation of diploid cells). Enamel matrix protein derivatives also include enamel matrix related polypeptides or proteins. The polypeptides or proteins may be bound to a suitable biodegradable carrier molecule, such as polyamine acids or polysaccharides, or combinations thereof. Furthermore, the term enamel matrix derivatives also encompass synthetic analogous substances.

Proteins are biological macromolecules constituted by amino acid residues linked together by peptide bonds. Proteins, as linear polymers of amino acids, are also called polypeptides. Typically, proteins have 50-800 amino acid residues and hence have molecular weights in the range of from about 6,000 to about several hundred thousand Dalton or more. Small proteins are called peptides, oligopeptides or polypeptides. In the context of the present invention, a "polypeptide fragment" for use in accordance with the present invention, refers to a polypeptide which may be, but is not limited to, being 1-50 amino acids in length, such as 5, 10, 15, 20, 25, 30, 35, 40, 41, 42, 43, 44, 45, 46, 47, 47, 48, 49 or 50 amino acids. Such polypeptides may also be longer than 50 amino acids.

Enamel matrix proteins are proteins that normally are present in enamel matrix, i.e. the precursor for enamel (Ten Cate: Oral Histology, 1994; Robinson: Eur. J. Oral Science, January 1998, 106 Suppl. 1:282-91), or proteins which can be obtained by cleavage of such proteins. In general, such proteins have a molecular weight below 120,000 Dalton and include amelogenins, non-amelogenins, proline-rich non-amelogenins and tuftelins.

Examples of proteins for use according to the invention are amelogenins, proline-rich non-amelogenins, tuftelin, tuft proteins, serum proteins, salivary proteins, ameloblastin, sheathlin, and derivatives thereof, and mixtures thereof. Moreover, other proteins for use according to the invention are found in the marketed product EMDOGAIN® (BIORA AB, Sweden).

EMDOGAIN® (BIORA AB, S-205 12 Malmo, Sweden) contains 30 mg enamel matrix protein (EMD), heated for 3 hours at about 80° C. in order to inactivate residual proteases, and 1 ml Vehicle Solution (Propylene Glycol Alginate), which are mixed prior to application, unless the protein and the vehicle are tested separately. The weight ratio is about 80/8/12 between the main protein peaks at 20, 14 and 5 kDa, respectively.

In general, the major proteins of an enamel matrix are known as amelogenins. They are markedly hydrophobic substances that under physiologically conditions form aggregates They may carry or be carriers for other proteins or peptides.

The LMW fraction and/or the enamel matrix polypeptide which is at least 80%, such as 90% identical to the amino acid sequence as shown in SEQ ID NO: 1 (TRAP63), a homologue, analogue, or a pharmaceutically acceptable salt thereof, which can stimulate the tissue formation phase of a wound healing process, as disclosed by the present invention may in the context of the present invention, be in a substantially isolated or purified form. It will be understood that the fractions, proteins, polypeptides, peptides and/or fragments thereof may be mixed with carriers or diluents or be comprised in a pharmaceutical composition, which will not interfere with the intended purpose of the proteins, polypeptides, peptides and/or fragments thereof and which will still be regarded as substantially isolated. Such a substantially purified form will generally comprise the Fraction consisting of and protein, polypeptide, peptide and/or fragment in a preparation in which more than 90%, e.g. 95%, 96%, 97%, 98% or 99% of the protein in the preparation is a fraction and/or a combined polypeptide fragment according to the invention.

By a protein, polypeptide, peptide and/or fragment thereof having an amino acid sequence at least, for example 95% identical to a reference amino acid sequence, is intended that the amino acid sequence of e.g. the polypeptide is identical to the reference sequence, except that the amino acid sequence may include up to 5 point mutations per each 100 amino acids of the reference amino acid sequence. In other words, to obtain a polypeptide having an amino acid sequence at least 95% identical to a reference amino acid sequence: up to 5% of the amino acids in the reference sequence may be deleted or substituted with another amino acid, or a number of amino acids up to 5% of the total amino acids in the reference sequence may be inserted into the reference sequence. These mutations of the reference sequence may occur at the amino and/or carboxy terminal positions of the reference amino acid sequence or anywhere between those terminal positions, interspersed either individually among amino acids in the reference sequence or in one or more contiguous groups within the reference sequence.

In the present invention, a local algorithm program is best suited to determine identity. Local algorithm programs, (such as Smith-Waterman) compare a subsequence in one sequence with a subsequence in a second sequence, and find the combination of subsequences and the alignment of those subsequences, which yields the highest overall similarity score. Internal gaps, if allowed, are penalized. Local algorithms work well for comparing two multidomain proteins, which have a single domain or just a binding site in common.

Methods to determine identity and similarity are codified in publicly available programs. Preferred computer program methods to determine identity and similarity between two sequences include, but are not limited to, the GCG program package (Devereux, J et al (1994)) BLASTP, BLASTN, and FASTA (Altschul, S. F. et al (1990)). The BLASTX program is publicly available from NCBI and other sources (BLAST Manual, Altschul, S. F et al, Altschul, S. F. et al (1990)). Each sequence analysis program has a default scoring matrix and default gap penalties. In general, a molecular biologist would be expected to use the default settings established by the software program used.

The proteins of an enamel matrix can typically be divided into a high molecular weight part and a low molecular weight part, which fraction contains acetic acid extractable proteins generally referred to as amelogenins (cf. EP-B-0 337 967 and EP-B-0 263 086).

By separating the proteins, e.g. by precipitation, ion-exchange chromatography, preparative electrophoresis, gel permeation chromatography, reversed phase chromatography or affinity chromatography, the different molecular weight amelogenins can be purified.

In general, the enamel matrix, enamel matrix derivatives and enamel matrix proteins are hydrophobic substances, i.e. less soluble in water, especially at increased temperatures In general, these proteins are soluble at non-physiological pH values and at a low temperature such as about 4-20° C., while they will aggregate and precipitate at body temperature (35-37° C.) and neutral pH.

In a specifically preferred embodiment, a formulation for use according to the present invention, thus comprises active enamel substances which at least partially are aggregated, and/or which after application in vivo are capable of forming aggregates. The particle size of said aggregates being in a range of from about 1 μm to about 20 nm, such as between 1 μm and 20 nm, 1 m and 10 nm, 5 μm and 10 nm, 10 μm and 1 nm, 100 μm and 10 nm, 100 μm and 1 nm, 1 μM and 1 nm, 1 μm and 5 nm, 1 μm and 15 nm.

In accordance with the present invention the isolated LMW fraction and/or the enamel matrix polypeptide which is at least 80%, such as 90% identical to the amino acid sequence as shown in SEQ ID NO: 1 (TRAP63), a homologue, analogue, or a pharmaceutically acceptable salt thereof, may be used together with other active drug substances such as, e.g. anti-bacterial, anti-inflammatory, antiviral, antifungal substances or in combination with local chemotherapy, inducers of apoptosis, growth factors such as, e.g., TGFβ, PDGF, IGF, FGF, EGF, keratinocyte growth factor or peptide analogues thereof. Enzymes—either inherently present in the enamel matrix or preparation thereof or added—may also be used in combination with an enamel matrix fraction and/or polypeptide fragment according to the present invention, especially proteases.

Pharmaceutical Compositions

Depending on the use of the LMW fraction and/or enamel matrix polypeptide which is at least 80%, such as 90% identical to the amino acid sequence as shown in SEQ ID NO: 1 (TRAP63), a homologue, analogue, or a pharmaceutically acceptable salt thereof according to the present invention, a composition may be a pharmaceutical and/or a therapeutic and/or a cosmetic composition. Presently, a pharmaceutical and/or therapeutic composition is also intended to embrace cosmetic compositions as well as compositions belonging to the so-called grey area between pharmaceuticals and cosmetics, namely cosmeceuticals.

A pharmaceutical and/or therapeutic composition comprising the LMW fraction and/or enamel matrix polypeptide which is at least 80%, such as 90% identical to the amino acid sequence as shown in SEQ ID NO: 1 (TRAP63), a homologue, analogue, or a pharmaceutically acceptable salt thereof according to the present invention, serves as a drug delivery system. In the present context the term "drug delivery system" denotes a pharmaceutical and/or therapeutic composition (a pharmaceutical and/or therapeutic formulation or a dosage form) that upon administration presents the active substance to the body of a human or an animal.

For the administration to an individual (such as an animal or a human), the LMW fraction and/or enamel matrix polypeptide which is at least 80%, such as 90% identical to the amino acid sequence as shown in SEQ ID NO: 1 (TRAP63), a homologue, analogue, or a pharmaceutically acceptable salt thereof according to the present invention, and/or a preparation thereof, are preferably formulated into a pharmaceutical composition containing the LMW fraction and/or enamel matrix polypeptide which is at least 80%, such as 90% identical to the amino acid sequence as shown in SEQ ID NO: 1 (TRAP63), a homologue, analogue, or a pharmaceutically acceptable salt thereof according to the present invention, and, optionally, one or more pharmaceutically acceptable excipients.

A composition comprising the LMW fraction and/or enamel matrix polypeptide which is at least 80%, such as 90% identical to the amino acid sequence as shown in SEQ ID NO: 1 (TRAP63), a homologue, analogue, or a pharmaceutically acceptable salt thereof according to the present invention, to be administered, may be adapted for administration by any suitable route, e.g. by systemic administration to a patient through a hose, syringe, spray or draining device.

Furthermore, a composition may be adapted to administration in connection with surgery, e.g. as a systemic administration by infusion into the blood, lymph, ascites, or spinal fluids, or by inhalation. For systemic application, the compositions according to the invention may contain conventionally non-toxic pharmaceutically acceptable carriers and excipients according to the invention, including microspheres and liposomes. Administration of a composition according to the present invention may also be performed via any other conventional administration route, such as, but not limited to, an oral, parenteral, intravenous, buccal, aural, rectal, vaginal, intraperitoneal, topical (dermal), or nasal route, or by the administration to a body cavity such as e.g. a tooth root or a tooth root canal.

Other applications may of course also be relevant such as, e. g., application on dentures, protheses, implants, and application to body cavities such as the oral, nasal and vaginal cavity. The mucosa may be selected from oral, buccal, nasal, aural, rectal and vaginal mucosa. Furthermore, the application may be directly on or onto a wound or other soft tissue injuries.

Furthermore, application within the dental/odontologic area is also of great importance. Relevant examples are application to periodontal (dental) pockets, to gingiva or to gingival wounds or other wounds located in the oral cavity, or in connection with oral surgery.

A composition for use in accordance with the present invention may be, but is not limited to, in the form of, e.g., a fluid, semi-solid or solid composition such as, but not limited to, dissolved transfusion liquids, such as sterile saline, Ringer's solution, glucose solutions, phosphate buffer saline, blood, plasma, water, powders, microcapsules, bioabsorbable patches, drenches, sheets, bandages, plasters, implants, pills, sprays, soaps, suppositories, vagitories, toothpaste, lotions, mouthwash, shampoo, microspheres, nanoparticles, sprays, aerosols, inhalation devices, solutions, dispersions, wetting agents, suspensions, emulsions, pastes, ointments, hydrophilic ointments, creams, gels, hydrogels (e.g. poly ethylene glycols), dressings, devices, templates, smart gels, grafts, solutions, emulsions, suspensions, powders, films, foams, pads, sponges (e.g. collagen sponges), transdermal delivery systems, granules, granulates, capsules, agarose or chitosan beads, tablets, microcapsules, freeze-dried powders, granules, granulates or pellets, and mixtures thereof.

Suitable dispersing or wetting agents for use in accordance with the invention, may be naturally occurring phosphatides, e.g., lecithin, or soybean lecithin; condensation products of ethylene oxide with e.g. a fatty acid, a long chain aliphatic alcohol, or a partial ester derivable from fatty acids and a hexitol or a hexitol anhydride, e.g. polyoxyethylene stearate, polyoxyethylene sorbitol monooleate, polyoxyethylene sorbitan monooleate, etc. The invention is however not limited thereto.

Suitable suspending agents are, e.g., naturally occurring gums such as, e.g., gum acacia, xanthan gum, or gum tragacanth; celluloses such as, e.g., sodium carboxymethylcellulose, microcrystalline cellulose (e.g. Avicel® RC 591, methylcellulose); alginates and kitosans such as, but not limited to, sodium alginate, etc.

A liquid composition, for use in accordance with the present invention, may e.g. be, but is not limited to, a solution, dispersion or suspension for application on a surface of e.g. a medical implant or device. Once applied, the composition should preferably solidify, e.g. by drying, to a solid or at least highly viscous composition which does not dissolve on storage or when the implant or device is in use.

Such a composition is preferably applied under sterile conditions and/or sterilised after application by irradiation or exposure to ethylene oxide gas. When the composition is in the form of a liquid composition, it may also be applied shortly before the medical implant or device is to be introduced into the body. As an alternative to applying a composition comprising a fraction(s) and/or polypeptide fragment(s) of an active enamel substance on the medical implant or device, the composition may be applied on a surface of a tissue which is in contact with the implant or device, such as a tissue comprising a substantial proportion of epithelial cells as indicated above. Furthermore, the composition may be applied on both the implant and/or device and on a tissue in contact therewith.

It should also be emphasized that any other pharmaceutical composition as disclosed by the present invention may be used for the application on a surface of a medical implant or device.

A composition according to the present invention, may also, in addition to what already has been disclosed herein, be formulated according to conventional pharmaceutical practice, see, e.g., "Remington's Pharmaceutical Sciences" and "Encyclopedia of Pharmaceutical Technology", edited by Swarbrick, J. & J. C. Boylan, Marcel Dekker, Inc., New York, 1988.

A pharmaceutically acceptable excipient is a substance which is substantially harmless to the individual to which the composition is to be administered. An excipient is comprised in a pharmaceutical composition according to the invention. Such an excipient normally fulfils the requirements given by the national health authorities. Official pharmacopoeias such as e.g. the British Pharmacopoeia, the United States of America Pharmacopoeia and The European Pharmacopoeia set standards for pharmaceutically acceptable excipients.

The choice of pharmaceutically acceptable excipient(s) in a composition, and the optimum concentration thereof, for use according to the invention, cannot generally be predicted and must be determined on the basis of an experimental evaluation of the final composition.

However, suitable excipients for the present purpose may be selected from such excipients that promote application of the composition comprising fraction(s) and/or polypeptide fragment(s) according to the present invention on a surface of the implant or device, or that promote the adherence of the composition to the surface on application, or that prevent immediate dissolution of the composition or protract the release of fraction(s) and/or polypeptide fragment(s) according to the present invention from the composition. A person skilled in the art of pharmaceutical formulation can find guidance in e.g., "Remington's Pharmaceutical Sciences", 18th Edition, Mack Publishing Company, Easton, 1990.

Whether a pharmaceutically acceptable excipient is suitable for use in a pharmaceutical composition is generally dependent on which kind of dosage form is chosen for use for a particular kind of wound, and/or any other type of disorder and/or damage to a body.

The pharmaceutically acceptable excipients may include solvents, buffering agents, preservatives, humectants, chelating agents, antioxidants, stabilizers, emulsifying agents, suspending agents, gel-forming agents, ointment bases, penetration enhancers, perfumes, powders and skin protective agents. It should however be emphasized that the invention is not limited thereto.

Examples of such solvents for use in a composition in accordance with the present invention, are water, alcohols, vegetable or marine oils (e.g. edible oils like almond oil, castor oil, cacao butter, coconut oil, corn oil, cottonseed oil, linseed oil, olive oil, palm oil, peanut oil, poppy seed oil, rape seed oil, sesame oil, soybean oil, sunflower oil, and tea seed oil), mineral oils, fatty oils, liquid paraffin, polyethylene glycols, propylene glycols, glycerol, liquid polyalkylsiloxanes, or other hydrophilic or etheric solvents such as weak acids with a pH of about 5.5-6.0 facilitating the subsequent application of filling materials in the tooth, as well as mixtures thereof.

Examples of buffering agents are citric acid, acetic acid, tartaric acid, lactic acid, hydrogen phosphoric acid, bicarbonates, phosphates, diethylamine etc.

Suitable examples of preservatives are parabens, such as methyl, ethyl, propyl p-hydroxybenzoate, butylparaben, isobutylparaben, isopropylparaben, potassium sorbate, sorbic acid, benzoic acid, methyl benzoate, phenoxyethanol, bronopol, bronidox, MDM hydantoin, iodopropynyl butylcarbamate, EDTA, benzalconium chloride, and benzylalcohol, or mixtures of preservatives.

Examples of humectants are glycerin, propylene glycol, sorbitol, lactic acid, urea, and mixtures thereof.

Examples of chelating agents are sodium EDTA and citric acid

Examples of antioxidants are butylated hydroxy anisole (BHA), ascorbic acid and derivatives thereof, tocopherol and derivatives thereof, cysteine, and mixtures thereof.

Examples of emulsifying agents are naturally occurring gums, e.g. gum acacia or gum tragacanth; naturally occurring phosphatides, e.g. soybean lecithin, sorbitan monooleate derivatives; wool fats; wool alcohols; sorbitan esters; monoglycerides; fatty alcohols; fatty acid esters (e.g. triglycerides of fatty acids); and mixtures thereof.

Examples of suspending agents are e.g. celluloses and cellulose derivatives such as, e.g., carboxymethyl cellulose, hydroxyethylcellulose, hydroxypropylcellulose, hydroxypropylmethylcellulose, microcrystalline cellulose, carraghenan, acacia gum, arabic gum, tragacanth, and mixtures thereof.

Examples of gel bases, viscosity-increasing agents or components which are able to take up exudate from a wound are: liquid paraffin, polyethylene, fatty oils, colloidal silica or aluminium, zinc soaps, glycerol, propylene glycol, tragacanth, carboxyvinyl polymers, magnesium-aluminium silicates, Carbopol®, hydrophilic polymers such as, e.g. starch or cellulose derivatives such as, e.g., carboxymethylcellulose, hydroxyethylcellulose and other cellulose derivatives, water-swellable hydrocolloids, carragenans, hyaluronates (e.g hyaluronate gel optionally containing sodium chloride), collagen, gelatine, pectin, chitosans and alginates including propylene glycol aginate.

In the present invention, the LMW fraction and/or enamel matrix polypeptide which is at least 80%, such as 90% identical to the amino acid sequence as shown in SEQ ID NO: 1 (TRAP63), a homologue, analogue, or a pharmaceutically acceptable salt thereof according to the present invention, can be incorporated into a polymeric matrix so that it is released by degradation of the polymeric matrix, by enzymatic action and/or by diffusion. Said polymeric matrix is either suitable for cellular in-growth, or cell-occlusive. Comprised in the invention is thus in particular a pharmaceutical and/or cosmetic formulation of the LMW fraction and/or enamel matrix polypeptide which is at least 80%, such as 90% identical to the amino acid sequence as shown in SEQ ID NO: 1 (TRAP63), a homologue, analogue, or a pharmaceutically acceptable salt thereof according to the present invention, at a low total concentration within the formulation, wherein a spatial and/or selective regulation of release of said active enamel substance permits a great percentage of the active enamel substance to be released at the time of appropriate cellular activity.

Consequently, one aspect of the present invention relates to a pharmaceutical and/or therapeutic formulation for administering the LMW fraction and/or enamel matrix polypeptide which is at least 80%, such as 90% identical to the amino acid sequence as shown in SEQ ID NO: 1 (TRAP63), a homologue, analogue, or a pharmaceutically acceptable salt thereof according to the present invention, comprising a polymeric matrix, either suitable for cellular growth, in-growth and/or migration, or being cell-occlusive, and a fraction and/or polypeptide fragment, wherein said matrix is formed by a nucleophilic addition reaction between a strong nucleophile and a conjugated unsaturated bond, or a conjugated unsaturated group.

Preferably, the conjugated unsaturated groups or conjugated unsaturated bonds are acrylates, vinylsulfones, methacrylates, acrylamides, methacrylamides, acrylonitriles, vinylsulfones, 2- or 4-vinylpyridinium, maleimides, or quinones.

Examples of ointment bases are e. g. beeswax, paraffin, cetanol, cetyl palmitate, vegetable oils, sorbitan esters of fatty acids (Span), polyethylene glycols, and condensation products between sorbitan esters of fatty acids and ethylene oxide, e. g polyoxyethylene sorbitan monooleate (Tween).

Examples of hydrophobic or water-emulsifying ointment bases are paraffins, vegetable oils, animal fats, synthetic glycerides, waxes, lanolin, and liquid polyalkylsiloxanes.

Examples of hydrophilic ointment bases are solid macrogols (polyethylene glycols)

Other examples of ointment bases are triethanolamine soaps, sulphated fatty alcohol and polysorbates.

Examples of powder components are: alginate, collagen, lactose, powder which is able to form a gel when applied to a wound (absorbs liquid/wound exudate). Normally, powders intended for application on large open wounds must be sterile and the particles present must be micronized.

Examples of other excipients are polymers such as carmelose, sodium carmelose, hydroxypropylmethylcellulose, hydroxyethylcellulose, hydroxypropylcellulose, methylcellulose, pectin, xanthan gum, locust bean gum, acacia gum, gelatin, carbomer, emulsifiers like vitamin E, glyceryl stearates, cetanyl glucoside, collagen, carrageenan, hyaluronates and alginates and kitosans.

Examples of diluents and disintegrating agents are but not limited to lactose, saccharose, emdex, calcium phosphate materials, such as calcium phosphate substrates, calcium phosphate carriers (comprising hydroxyapatite, bi-phasic calcium phosphates, and tri-calcium phosphates), calcium carbonate, calcium sulphate, mannitol, starches and microcrystalline cellulose.

Examples of binding agents are, but not limited to, saccharose, sorbitol, gum acacia, sodium alginate, gelatine, starches, cellulose, sodium coboxymethylcellulose, methylcellulose, hydroxypropylcellulose, polyvinylpyrrolidone and polyetyleneglycol.

Compositions which have proved to be of importance in connection with topical application are those which have tixothropic properties, i.e. the viscosity of the composition is affected e.g. by shaking or stirring so that the viscosity of the composition at the time of administration can be reduced and when the composition has been applied, the viscosity increases so that the composition remains at the application site.

However, it is appreciated that in those cases where a pharmaceutically acceptable excipient may be employed in different dosage forms or compositions, the application of a particular pharmaceutically acceptable excipient is not limited to a particular dosage form or of a particular function of the excipient.

In a toothpaste or mouthwash formulation or other formulation for application to teeth or tooth roots, fraction(s) and/or polypeptide fragment(s) according to the present invention may either be present in a dissolved state in a vehicle of slightly acid pH or as a dispersion in a vehicle of neutral pH. It is anticipated that fraction(s) and/or polypeptide fragment(s) according to the present invention may form a protective layer on the surface of the teeth, thereby preventing the attachment of caries producing bacteria. In such dental care preparations, the fraction and/or polypeptide fragment may be formulated together with one or more other compounds which have a caries preventive effect, notably fluorine or another trace element such as vanadium or molybdenum. At neutral pH, the trace element is believed to be bound to (e. g. by ion bonds) or embedded in the active enamel substance from which it is released to exert its caries preventive effect when the fraction and/or polypeptide fragment is dissolved at a pH of about 5.5 or less, e. g. due to acid production by caries producing bacteria.

In a pharmaceutical composition for use according to the invention, the LMW fraction and/or enamel matrix polypeptide which is at least 80%, such as 90% identical to the amino acid sequence as shown in SEQ ID NO: 1 (TRAP63), a homologue, analogue, or a pharmaceutically acceptable salt thereof according to the present invention is generally present in a concentration ranging from about 0.01% to about 99.9% w/w. The amount of composition applied will normally result in an amount of total protein per $cm^2$ area of dental pulp corresponding to from about 0.005 $mg/mm^2$ to about 5 $mg/mm^2$ such as from about 0.01 $mg/mm^2$ to about 3 $mg/mm^2$.

In those cases where the LMW fraction and/or enamel matrix polypeptide which is at least 80%, such as 90% identical to the amino acid sequence as shown in SEQ ID NO: 1 (TRAP63), a homologue, analogue, or a pharmaceutically acceptable salt thereof according to the present invention is administered in the form of a liquid composition, the concentration of the LMW fraction and/or enamel matrix polypeptide which is at least 80%, such as 90% identical to the amino acid sequence as shown in SEQ ID NO: 1 (TRAP63), a homologue, analogue, or a pharmaceutically acceptable salt thereof according to the present invention in the composition is in a range corresponding to from about 0.01 to about 50 mg/ml, e.g. from about 0.1 to about 30 mg/ml. Higher concentrations are in some cases desirable and can also be obtained such as a concentration of at least about 100 mg/ml.

LEGENDS TO FIGURES

Figure 6:
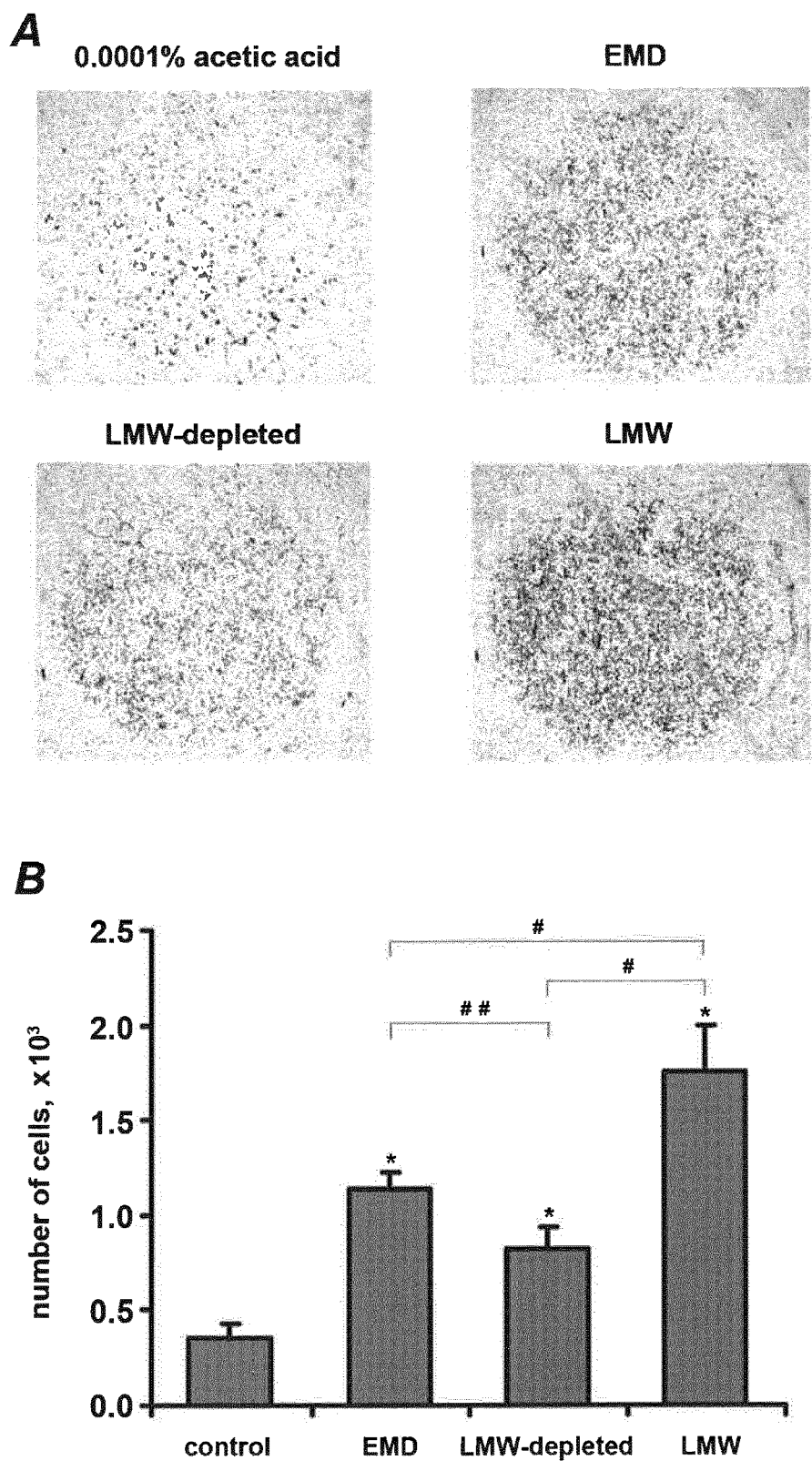
Figure 7:
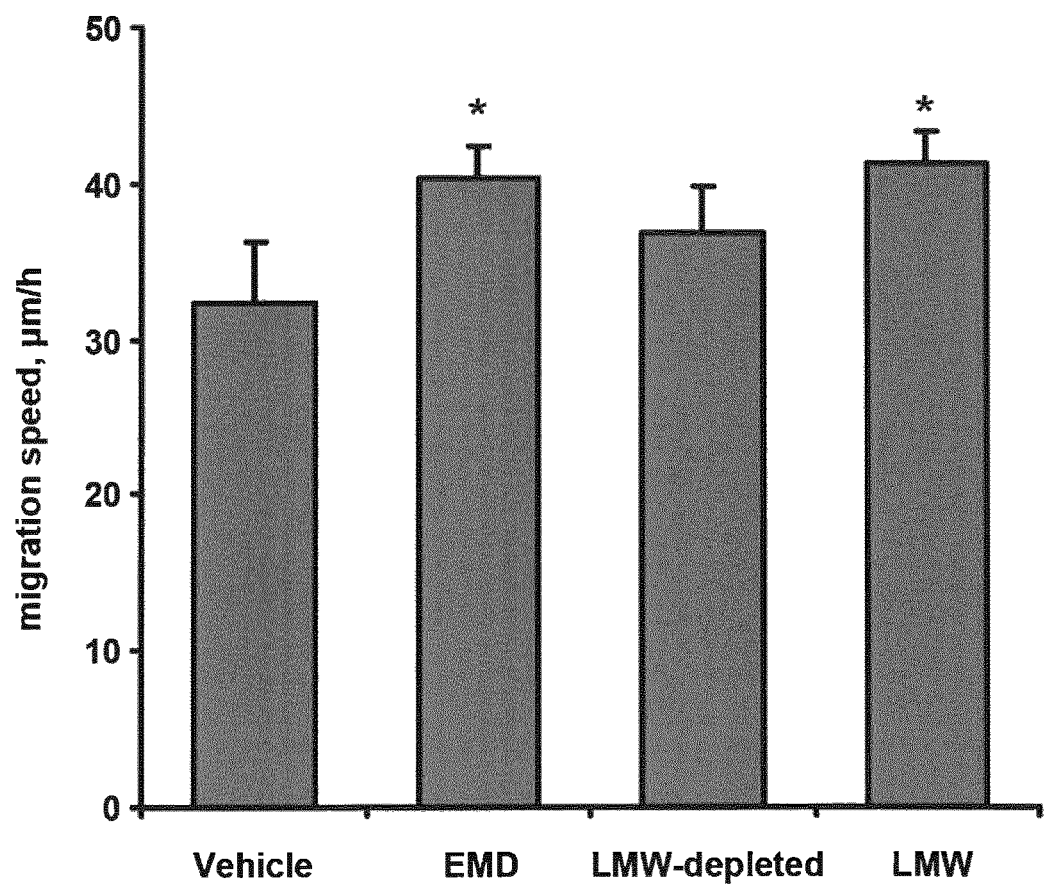
Figure 8:
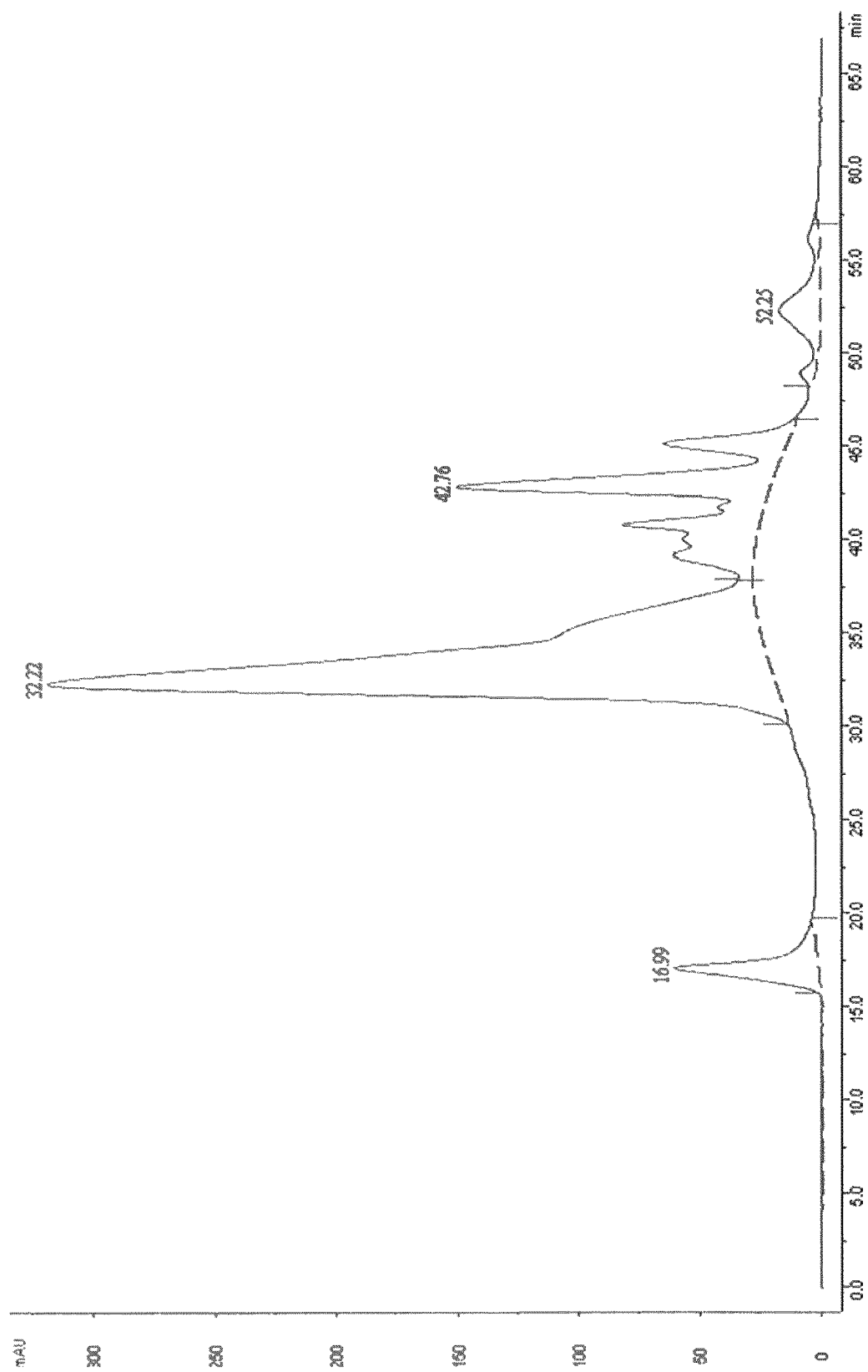
Figure 9:
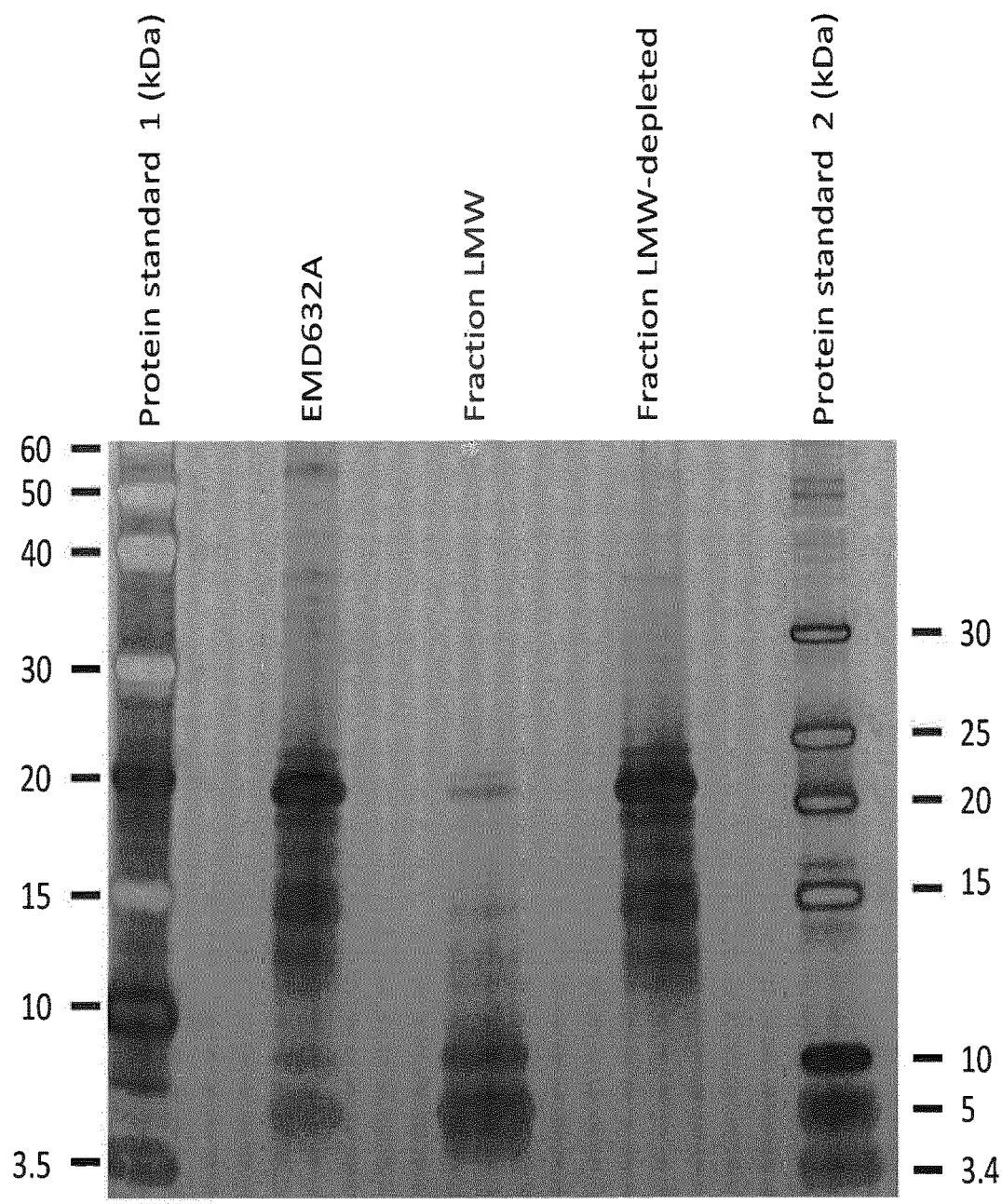
Figure 10:
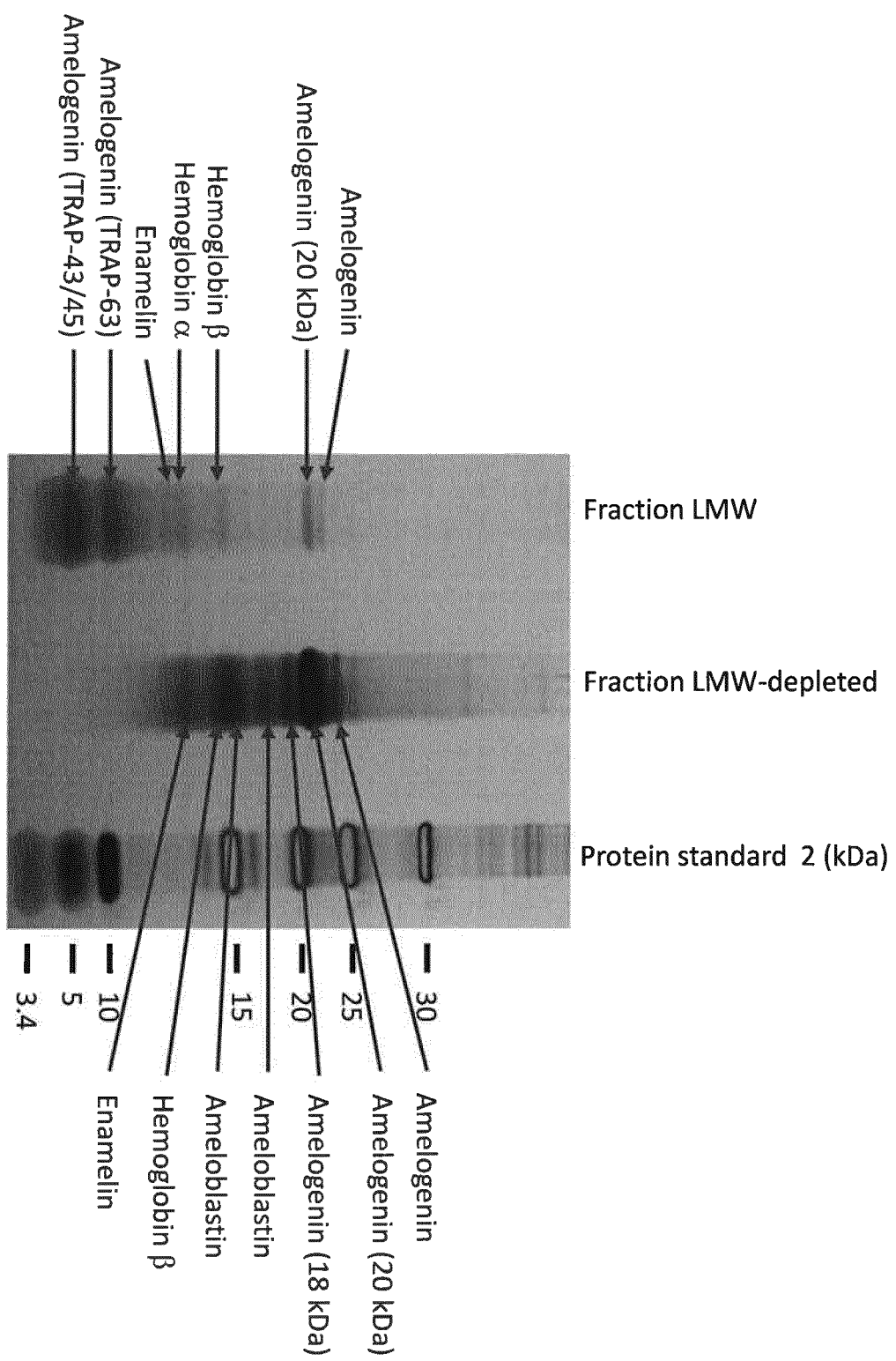

FIG. 1:
Effect of EMD and EMD Fractions on HUVEC Viability
Effect of EMD and EMD fractions on proliferation/viability of HUVECs determined by MTT assay. HUVECs were treated for 24 h with 10 μg/ml and 100 mg/ml EMD (A) and EMD fractions LMW-depleted (B) and LMW (C). Each value represents mean±S.E.M of five independent assays. The values of optical density (OD) of the different concentrations were normalized with the average value of the OD of vehicle control (=1).
significantly higher than control with P<0.01
* significantly lower compared to control with P<0.01
FIG. 2:
Effect of EMD and EMD Fractions on the Expression of E-Selectin and ICAM-1
Relative expression level of E-selectin (A) and ICAM-1 (B) genes upon incubation with EMD or EMD fractions LMW-depleted and LMW for 24 h. GAPDH was used as endogenous control gene. Each value represents mean±S.E.M. of six independent assays. ECM supplemented with 0.001% acetic acid served as vehicle control (=1).
* significantly higher compared to vehicle control with P<0.01.
significantly different between groups, P<0.05.
FIG. 3:
Effect of EMD and EMD Fractions on Surface Expression of ICAM-1
HUVECs were stimulated with EMD or EMD fractions LMW-depleted and LMW for 24 h. and stained with anti-ICAM-1 antibody. Mean fluorescence intensity (m.f.i.) values of cells stained with ICAM-1 antibodies were corrected for unspecific staining by subtracting the fluorescence of cells stained with the isotype control antibody
* significantly higher compared to vehicle control with P<0.01.
significantly different between groups, P<0.05.
FIG. 4:
Effect of EMD and EMD Fractions on the Expression of VEGF Flt-1 and KDR
A, B—relative expression level of Flt-1 (A) and KDR (B) genes upon incubation with EMD or EMD fractions LMW-depleted and LMW for 24 h. GAPDH was used as endogenous control gene. Each value represents mean±S.E.M. of six independent assays. ECM supplemented with 0.001% acetic acid served as vehicle control (=1). C, D—percentage of Flt-1 and KDR positive cells measured by flow cytometry.
* significantly higher compared to vehicle control with P<0.01.
significantly different between groups, P<0.05.
FIG. 5:
Effect of EMD and EMD Fractions on the Expression of Angiopoietin-2 and vWF
A, B—relative expression level of angiopoietin-2 (A) and von Willebrand factor (B) genes upon incubation with EMD or EMD fractions LMW-depleted and LMW for 24 h. GAPDH was used as endogenous control gene. Each value represents mean±S.E.M. of six independent assays. ECM supplemented with 0.001% acetic acid served as vehicle control (=1). C, D—the levels of ang-2 and vWF proteins in conditioned media measured by commercially available ELISA.
* significantly higher compared to vehicle control with P<0.01.
significantly different between groups, P<0.05.
FIG. 6.
Effect of EMD and EMD Fractions on the Migration of HUVECs Measured in the Microchemotaxis Chamber.
Original photo (A) and cell number (B) showing the migration of HUVECs through the 8 μm polycarbonate filter depending on stimulation with EMD, LMW-depleted, and LMW at a concentration of 10 μg/ml for 8 hours. Stimulation with 0.0001% of acetic acid served as control.
* significantly higher compared to control with P<0.01.
significantly different between LMW vs. EMD and LMW vs. LMW-depleted, P<0.01.
significantly different between EMD vs. LMW-depleted, P<0.01.
FIG. 7.
Effect of EMD and EMD Fractions on the Migration Speed of HUVECs in the Time Lapse Microscopy Experiments.
The migration speed of HUVECs was determined in the time lapse microscopy experiments within the time interval from 12 to 24 h after seeding. Data are presented as mean±s.e.m. of three independent experiments.
* significantly higher compared to control with P<0.05
FIG. 8.
Representative SEC-HPLC chromatogram of EMD 632A and its complementary Low Molecular Weight (LMW) and Low Molecular Weight-depleted (LMW-depl) fractions.
FIG. 9.
SDS-PAGE of EMD632A and fractions LMW and LMW-depl. 0.8-1-1 μg protein were applied on each lane. Lane 1, Novex® Sharp protein Standard, numbers are in kDa; lane 3, EMD632A (0.8 μg); lane 5, fraction LMW (0.8 μg); lane 7, fraction LMW-depleted (1.1 μg); lane 9, Standard PageRuler low range, numbers are in kDa; lane 2, 4, 6, and 8 were left empty (filled with buffer).
FIG. 10.
Identity of proteins in EMD fractions LMW and LMW-depleted
FIG. 11.
Maldi spectrum of LMW; from top: full scan, zoom scan and zoom 1
FIG. 12.
Maldi spectrum of fraction LMW-depl; full scan and zoom scan

EXPERIMENTAL SECTION

Experiment 1

In the present study two EMD fractions with different molecular weight protein components were separated and their effect on human umbilical vein endothelial cells (HUVECs) was investigated in vitro. Fraction Low-Molecular Weight (LMVV) included proteins with a molecular weight (M.W.)<8 kDa. Fraction LMW-depleted included proteins with M.W. >8 kDa and lower than approximately 55 kDa. The effect of EMD fractions on viability, migration and expression of angiopoetin-2 (ang-2), von Willebrand factor (vWF), E-selectin, intracellular adhesion molecules 1 (ICAM-1), vascular endothelial growth factor (VEGF) receptors Flt-1 and KDR was investigated. The viability of HUVECs was inhibited by both LMW and LMW-depleted at concentrations 100 μg/ml, whereas EMD slightly increased cell viability. All stimuli induced a significant increase of the expression levels of E-selectin and ICAM-1. The effects of EMD and LMW-depleted on the expression of these proteins were markedly higher than that of LMW. The expression of VEGF-receptors Flt-1 and KDR was up-regulated by EMD and LMW and only marginally affected by LMW-depleted. The expression of ang-2 was significantly increased by EMD and not influenced by LMW and LMW-depleted. The expression of vWF was significantly increased by LMW and EMD but not affected by LMW-depleted. HUVECs migration was stimulated more strongly by LMW than by EMD and LMW-depleted. The in vitro study shows that the proteins composing EMD vary in their biological activity and positively affect different phases of angiogenesis and wound healing.

Material and Methods

Cells and Materials

Commercially available HUVECs pooled from 10 different healthy donors (Technoclone, Vienna, Austria) were used in the present study. HUVECs were cultured in endothelial cell medium (ECM, Technoclone, Austria) with 20% fetal bovine serum (FBS) supplemented with 100 U/ml penicillin, 100 μg/ml streptomycin, 0.25 μg/ml fungizone, 2 mM L-glutamine, 5 U/ml heparin and 30-50 μg/ml endothelial cell growth supplement in culture flasks coated with 0.2% gelatine at 37° C. in a humidified atmosphere of 5% $CO_2$ and 95% air The HUVECs from the $4^{th}$ to $7^{th}$ passage in culture were used.

EMD Separation

EMD fractions LMW and LMW-depleted were separated and purified by Institut Straumann using a modification of previously described methods. Briefly, EMD fractions LMW and LMW-depleted were extracted from porcine enamel matrix derivative via size exclusion high-performance liquid chromatography (Shodex KW 2003, Brechbühler A G, Switzerlandy) in 100 mM Na acetate pH 3.5 containing 100 mM NaCl. Lyophilized fractions were reconstituted in 0.1% acetic acid to produce a 10 mg/ml stock solution. Further dilutions of proteins (1-100 μg/ml) were performed into serum-free ECM.

The working solution of 100 μg/ml EMD or EMD fractions contained 0.001% of acetic acid, which did not exert any significant effect on any parameter investigated in this study Cell Proliferation/Viability For the proliferation/viability assay 3,4,5-dimethylthiazol-2-yl-2,5-diphenyl tetrazolium bromide (MTT) dye was used. HUVECs were seeded in 24-well plates coated with 0.2% gelatine at a density of $5 \times 10^4$ cells per well in 0.5 ml of ECM supplemented with 20% FBS. After 24 h, the medium in test wells was replaced by FBS-free ECM conditioned with EMD, LMW-depleted or LWM at concentrations of 1-100 μg/ml. Wells, stimulated with serum free ECM supplemented with 0.001% of acetic acid served as vehicle controls. After 24 h incubation, 100 μl of MTT solution (5 mg/ml in PBS) were added into each well and culture plates were incubated at 37° C. for 4 h. The medium was removed and 500 μl dimethylsulfoxide (DMSO) were added to each well, followed by 5 min incubation on a shaker. Finally, 100 μl of each cultured solution were transferred to a separate 96-well plate and the optical density (OD) was measured at 570 nm with an ELISA Reader (Molecular Devices, USA).

Chemotaxis Assay

Cell migration was assessed in a 48-well microchemotaxis chamber (Neuroprobe, Gaithersburg, Md., USA) on a polycarbonate filter with 8 μm pore size as described previously (Qu Z, Laky M, Ulm C, Matejka M, Dard M, Andrukhov O, Rausch-fan X. Effect of Emdogain on proliferation and migration of different periodontal tissue-associated cells. Oral Surg Oral Med Oral Pathol Oral Radiol Endod 2010; 109(6):924-31.). The chamber consisted of acrylic top and bottom plates, each containing 48 matched wells. Top and bottom plates were separated by a polycarbonate filter with 8 μm pore size (Neuroprobe, Gaithersburg, Md., USA). 26 μl of FBS-free medium containing EMD or EMD fractions (10 μg/ml) were filled in wells of the bottom plate. Wells filled with medium containing 0.0001% of acetic acid served as control. Subsequently, the bottom plate was covered with a filter and the top plate was applied so that each well corresponded to that of the bottom plate. A cell suspension containing $1 \times 10^4$ cells in 50 μL FBS-free medium was added to each well of the top plate and the whole chamber was incubated at 37° C. in humidified air with 5% $CO_2$ for 8 h. After incubation, cells on the upper surface of the filter were removed over the wiper blade and the filters were then fixed with methanol and stained with Hemacolor® for microscopy (Merck, Darmstadt, Germany). The cells migrated across the filter were counted under a light microscope at high-power magnification (×100) to measure transmigration in each well. Four fields were counted in each well and the total number was calculated. Four wells were used for each group; experiments were repeated in triplicate.

Cell Motility Measurements by Time Lapse Microscopy

HUVECs were harvested by trypsinisation and stained with Cell Tracker Orange CMRA (Molecular Probes, lnvitrogen, UK) according to the manufacturer's instructions. After staining and wash-out steps, cells were seeded in 4-well plate pre-coated with 0.2% gelatine at a density of $2*10^4$ cells pro well in 0.8 ml of ECM. In each experiment, one well was supplemented with 0.001% acetic acid and was used as a vehicle control, whereas other three wells contained EMD, LMW-depleted, or LMW at a concentration of 25 μg/ml. Then cells were incubated in an individually designed 37° C. temperature-controlled incubation chamber supplied with 5% $CO_2$ which was attached to an upright fluorescence microscope (Nikon Eclipse E 800M microscope; Nikon Instruments Europe B.V, Badhoevedorp, Netherlands). Fluorescently labeled cells were observed dynamically and photographed with a digital imaging system (Photometrics® Cascade 512F, Germany) every 30 min for 120 hours and cell behavior was recorded by making time-lapse movies with the aid of Lucia imaging analysis software (NIS-Elements AR, Nikon). Cell motility was analysed using tracking module by manual tracking mode. For each experiment 15 randomly selected cells pro well/group were tracked in the time period from 12 h until 24 h after seeding. Cell motility was described by average migration speed.

Measurements of Gene Expression Levels by Quantitative Real Time PCR

The effect of EMD fractions on mRNA expression levels of E-selectin, ICAM-1, Flt-1, KDR, ang-2, and vWF were determined by qPCR similarly to the method described previously [20, 21], taking the GAPDH encoding gene as internal reference. HUVECs were seeded in 24-well plates similar to MTT experiments and stimulated in serum free ECM with EMD, LMW-depleted fraction, or LWM fraction at concentrations of 10 and 100 mg/ml. Some wells were stimulated with FBS-free ECM supplemented with 0.001% of acetic acid and served as vehicle control. Isolation of total cellular mRNA and transcription into cDNA was performed using the TaqMan® Gene Expression Cells-to-CT™ kit (Ambion/Applied Biosystems, CA, USA) according to manufacturer's instructions). Real-time PCR was performed on an Applied Biosystems Step One Plus real-time PCR system (Applied Biosystem, CA, USA) using Taqman® gene expression assays with the following ID numbers (all from Applied Biosystems, CA, USA): E-selectin, Hs00174057_m1; ICAM-1, Hs00164932_m1; Flt-1, Hs01052961; KDR-1, Hs00911700_m1; ang-2, Hs01048043_m1; vWF, Hs00169795_m1; GAPDH, Hs99999905_m1). Duplicate PCR reactions were prepared and the point at which the PCR product was first detected above a fixed threshold (termed cycle threshold, $C_t$), was determined. Changes in the expression of target genes were calculated using $2^{-\Delta\Delta Ct}$ method, where $\Delta\Delta C_t\Delta\Delta C_t = (C_t^{target} - C_t^{GAPDH})_{sample} - (C_t^{target} - c)_t^{GAPDH})_{vehicle\ control}$, taking samples treated with 0.001% of acetic acid as a vehicle control.

Measurements of Cell Surface Protein Expression by Flow Cytometry.

The expression of adhesion molecules ICAM-1 and E-selectin as well as VEGF receptors Flt-1 and KDR on the cell surface of HUVECs was measured by fluorescence flow cytometry (Andrukhov O, Steiner I, Liu S, Bantleon H P, Moritz A, Rausch-Fan X. Different effects of *Porphyromonas gingivalis* lipopolysaccharide and TLR2 agonist Pam3CSK4 on the adhesion molecules expression in endothelial cells. Odontology 2014.). For the measurements of ICAM-1 and E-selectin expression, cells were stained with one of the following monoclonal antibodies conjugated with phycoerythrin (all eBioscience, San Diego, Calif., USA): mouse anti-human ICAM-1 antibody, mouse anti-human E-selectin antibody, and isotype control antibody. Surface expression of different proteins was analyzed using a flow cytometer (FACScan, Becton Dickinson, San Jose, Calif., USA). Cell counting was limited by 50000 events and the mean fluorescence intensities values were determined for each sample. The expression of ICAM-1 and E-selectin for each sample was quantified using Cell Quest software (Becton Dickinson, San Jose, Calif., USA) based on mean fluorescence intensity values of cells stained with ICAM-1 and E-selectin antibodies, which corrected for unspecific staining by subtracting the fluorescence of cells stained with the isotype control antibody (Pasceri V, Willerson J T, Yeh E T. Direct proinflammatory effect of C-reactive protein on human endothelial cells. Circulation 2000; 102(18):2165-8.). For the measurements of Flt-1 and KDR expression cells were stained with primary rabbit polyclonal antibodies and subsequently with secondary goat anti-rabbit antibody conjugated with phycoerythrin (all Santa Cruz Biotechnology, Dallas, Tex., USA). The percentage of Flt-1- and KDR-positive cells was analyzed by Cell Quest software (Becton Dickinson, San Jose, Calif., USA).

ELISA Analysis

Commercially available ELISA kits were used for measurements of vWF (Novateinbio, Woburn, Mass., USA) and ang-2 (RayBiotech, Inc., Norcross Ga., USA) in the conditioned media. For the measurement of vWF and ang-2 the samples were diluted by the ratio 1:20 and 1:10, respectively.

Statistical Analysis

The normal distribution of all data was tested with Kolmogorov-Smirnov test. After confirming normal distribution, the statistical differences between different groups were analysed by one-way analysis of variance (ANOVA) for repeated measures followed by t-test. All statistical analysis was performed using statistical program SPSS 19.0 (SPSS, Chicago, Ill., USA). Data are expressed as mean±S.E.M. Differences were considered to be statistically significant at $p<0.05$.

Results

Cell Viability

The effect of EMD and EMD fractions on the viability of HUVECs is shown in FIG. 1 Treatment of HUVECs with EMD at a concentration of 100 µg/ml increased viability significantly compared to lower EMD concentrations (FIG. 1A). In contrast, EMD fractions LMW-depleted and LMW both inhibited HUVECs viability significantly at 100 µg/ml and 10-100 µg/ml respectively (FIGS. 1B and C).

Expression of ICAM-1 and E-Selectin

Figure 2:
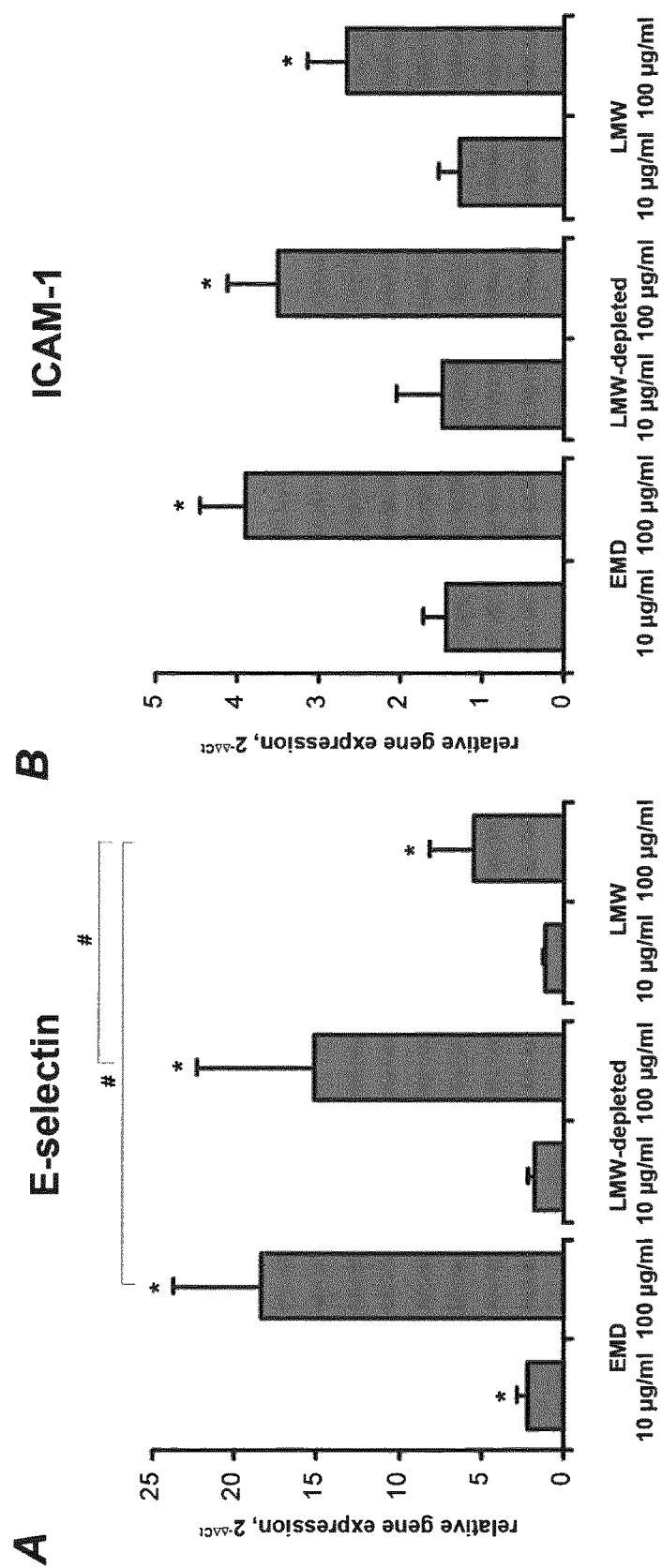
Figure 3:
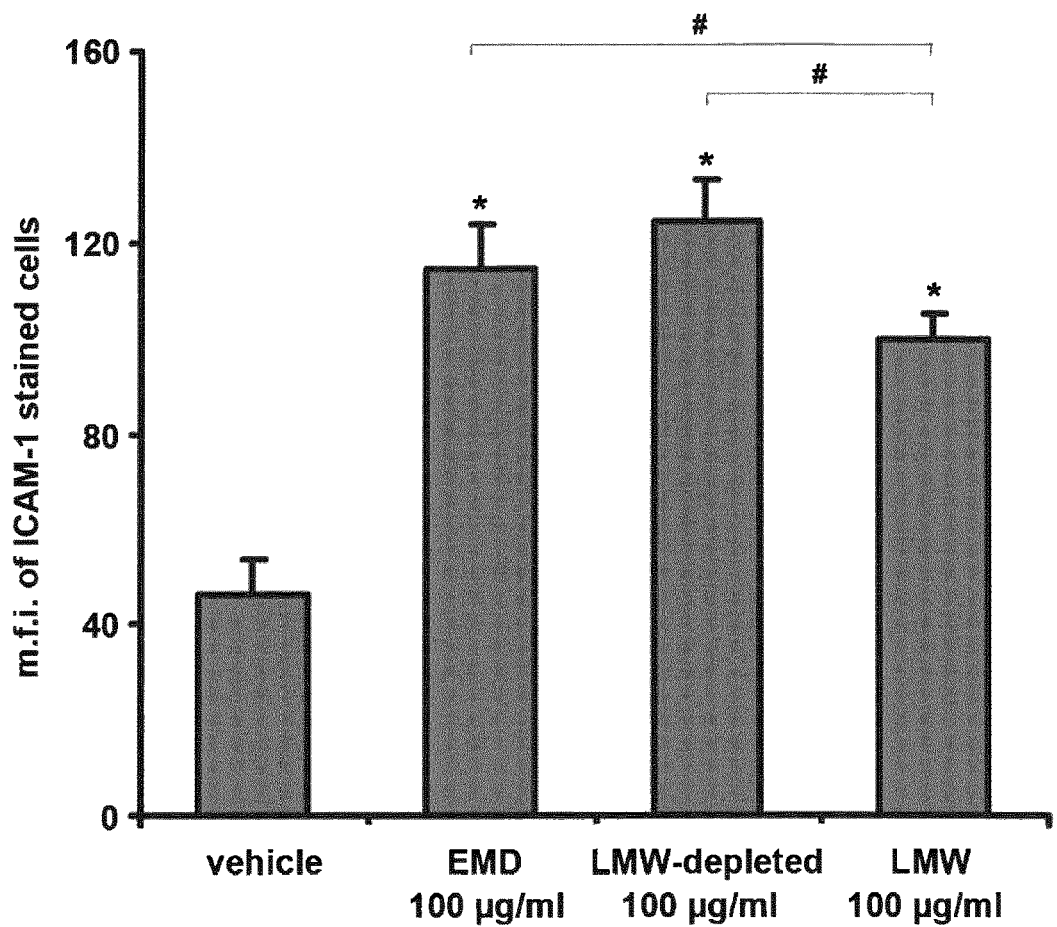

EMD and EMD fractions LMW-depleted and LMW at concentrations of 100 µg/ml induced a significant increase in the expression levels of adhesion molecules E-selectin and ICAM-1 (FIG. 2). The effect of EMD and LMW-depleted on the expression of E-selectin was about 3 times higher ($p<0.05$, FIG. 2a) than that of LMW. An increase in the ICAM-1 expression after stimulation with either EMD or LMW-depleted was about 1.5 times higher than after stimulation with LMW, but this difference was not statistically significant (FIG. 2b). The expression of E-selectin was also up-regulated by EMD at concentration of 10 µg/ml, whereas LMW-depleted and LMW at this concentration has no significant effect on E-selectin expression. All substances at concentration of 10 µg/ml had no significant effect on ICAM-1 expression.

The effect of EMD and EMD fractions on the surface expression of ICAM-1 is shown on the FIG. 3. The surface expression of ICAM-1 was significantly increased after stimulation with all substances at concentrations of 100 µg/ml ($p<0.01$). The effect of EMD and LMW-depleted on ICAM-1 expression was significantly higher than that of LMW ($p<0.05$). No surface expression of E-selectin was detected after 24 h stimulation: the fluorescence intensity of HUVECs stained with E-selectin antibody was not different from that of cells stained with isotype control antibody (data not shown).

Expression of VEGF Receptors Flt-1 and KDR

The effects of EMD and EMD fractions LMW-depleted and LMW on the expression of VEGF receptors Flt-1 and KDR were determined in HUVECs (FIG. 4). The expression levels of Flt-1 were significantly up-regulated by all substances at the concentration of 100 µg/ml ($p<0.05$, FIG. 4a). However, the effect of LMW was about 1.5 times higher than that of LMW-depleted ($p<0.05$, FIG. 4a). The expression of KDR was significantly increased after stimulation with either EMD or LMW at a concentration of 100 µg/ml ($p<0.05$, FIG. 4a). In contrast, stimulation with LMW-depleted at concentration of 100 µg/ml has no significant effect on KDR expression. All substances at concentrations of 10 µg/ml have no significant effect on the expression of Flt-1 and KDR. The percentage of Flt-1 and KDR positive cells was significantly increased by both EMD and EMD fractions LMW-depleted and LMW in concentrations of 100 µg/ml (FIGS. 4c and 4d). The effect of LMW on the surface expression of both Flt-1 and KDR was significantly higher compared to that of LMW-depleted ($p<0.05$).

Expression of ang-2 and vWF

Ang-2 mRNA expression levels were significantly increased in a dose-dependent manner by pretreatment of HUVECs with EMD (FIG. 5a). Ang-2 expression was also slightly increased by LWM-depleted at concentration of 100 µg/ml, but this effect was not statistically significant. LMW had no influence on ang-2 expression. The levels of ang-2 in conditioned media was significantly increased upon stimulation with EMD at a concentration of 100 µg/ml, but not affected by LMW-depleted and LMW (FIG. 5c). vWF expression in HUVECs was increased by EMD and LMW at concentration of 100 μg/ml (FIG. 5b), whereas no effect of LMW-depleted on the expression of this protein was observed. The effect of LMW on the gene-expression level of vWF was significantly higher than that of EMD and LMW-depleted (FIG. 5b). All substances at concentration of 10 μg/ml had no significant effect on the expression of vWF. The levels of vWF in conditioned media were significantly increased by EMD and LMW at a concentration of 100 μg/ml (FIG. 5d). The vWF production by HUVECs upon stimulation with LMW was significantly higher compared to stimulation with LMW-depleted.

Chemotaxis Assays

The representative photos of cells migrated through the 8 μm polycarbonate membrane and the quantitative evaluation of this chemotaxis assay are presented in FIG. 6. EMD as well as EMD fractions stimulated migration of HUVECs (p<0.01). The strongest chemoattractant ability was observed for LMW, followed by EMD and LMW-depleted. The number of cells migrated through the membrane after stimulation with LMW was about 1.5 and 2 times higher than that after stimulation with EMD and LMW-depleted, respectively (p<0.01).

Time Lapse Microscopy

The effect of of EMD and EMD fractions LMW-depleted and LMW on HUVECs migration speed in time lapse microscopy experiments is shown on the FIG. 7. The migration speed of HUVECs was significantly higher upon stimulation with EMD or LMW was significantly higher compared to vehicle control. The migration speed of cells stimulated with EMD and LMW also tended to be higher compared to cells stimulated with LMW-depleted, however these differences were not statistically significant.

Discussion

Knowledge about the exact physiological effects of different EMD protein is important for development of new EMD-based products and further improvement of periodontal therapy outcomes. Furthermore, development of new EMD based products might allow reducing the therapy costs, which is currently one of the limiting factors of EMD application in the clinic.

In the present study two EMD fractions were separated by size exclusion chromatography and their effect on the viability and differentiation of human umbilical vein endothelial cells was investigated in vitro. Fraction LMW-depleted comprised the proteins with a molecular weight of 8 to approximately 55 kDa. The major component of this fraction is the 20 kDa amelogenin. Fraction LMW contained mainly enzymatically degraded amelogenin peptides with a molecular weight <8 kDa. Endothelial cells were used because these cells play a primary role in the process of angiogenesis, which is a crucial factor during the wound healing process because formation of new vasculature is necessary for delivery of oxygen, cells and nutrients to the wound sites. The effects of EMD fraction on proliferation/viability, migration, and the expression of several proteins potentially involved in angiogenesis and wound healing were investigated.

The viability of HUVECs was significantly decreased after treatment with fractions LMW-depleted and LMW and slightly increased by EMD at 100 μg/ml. The reasons for the different effect of EMD and EMD fractions on cell viability are not entirely clear. It is plausibly to assume that some EMD components might decrease HUVECs proliferation. The total amount of these components could be higher in EMD fractions than in EMD itself. This assumption might explain different effect of EMD fractions and EMD on HUVECs proliferation/viability. Previous studies show controversial results about the effect of EMD on endothelial cells viability. This discrepancy could be due to different cell sources, experimental protocols, and different EMD lots used in these studies.

Particularly, initial seeding density could be an important parameter influencing the direction of EMD effect on endothelial cells proliferation, because even a small increase of the seeding density might drastically inhibit proliferation of endothelial cells. Another important parameter influencing HUVECs proliferation is the concentration of FBS during stimulation.

Both fractions LMW-depleted and LMW induced the gene expression of adhesion molecules E-selectin and ICAM-1 in HUVECs. However, only for ICAM-1 the changes observed on gene expression level correlated with the surface protein expression. In contrast, E-selectin protein could not be detected on HUVECs surface. This discrepancy might suggest that E-selectin expression is regulated also on translational level. This hypothesis is supported by observation that the expression of E-selectin in HUVECs upon stimulation with lipopolysaccharide is continuously up-regulated on mRNA level and only transiently increased on protein level (O.A., manuscript in preparation). Nevertheless, increase of E-selectin mRNA might suggest activation of a pro-inflammatory pathway in HUVECs. The effect of LMW-depleted on the expression of adhesion molecules was higher than that of LMW and comparable to that of EMD. E-selectin and ICAM-1 mediate the adhesion of inflammatory cells to the endothelium and their migration to wound sites. Therefore, the present data suggest that proteins of LMW-depleted fraction might be important for the inflammatory phase of wound healing. Amelogenin is the main component of fraction LMW-depleted and presents itself as the most promising candidate for inducing the adhesion molecule expression in HUVECs. This hypothesis is supported by an animal study, which showed that amelogenin gene splice products induce recruitment of inflammatory cells into pulp of mice. The mechanisms by which EMD and/or amelogenin affect adhesion molecule expression are currently under investigation. A possible mechanism might involve activation of ERK-1/2, which is known to control the expression of E-selectin and ICAM-1. A recent in vitro study on odontoblasts showed that amelogenin induced activation of ERK-1/2 kinase, but the significance of this pathway in endothelial cells needs to be verified.

The increase of VEGF receptor Flt-1 and KDR expression by treatment of HUVECs with EMD was showed for the first time in this study. VEGF is a crucial regulator of angiogenesis and increased expression of VEGF receptors in endothelial cells leads to activation of angiogenesis. It may therefore be speculated that EMD-induced increase of VEGF receptor gene expression may play an important role in the regeneration of the periodontium. Some previous in vitro studies showed that EMD induced the production of VEGF by cells of the periodontium, particularly human gingival fibroblasts and periodontal ligament cells. Enhanced production of VEGF by cells of the periodontium in response to EMD on the one hand, and the increase in the expression of VEGF receptors in endothelial cells on the other hand might be important mechanisms underlying the ability of EMD proteins to orchestrate periodontal healing process in vivo. These proposed mechanisms of EMD effects in vivo are supported by a recent clinical study in which the application of Emdogain onto the root surface and into the periodontal pocket resulted in the increase of VEGF expression and microvessel density in gingival tissues. The present data suggest that EMD low molecular weight proteins are responsible for the up-regulation of VEGF receptor expression and play an important role in periodontal wound healing.

EMD induced a significant increase in the expression of ang-2. A similar tendency was also observed for LMW-depleted. In contrast no effect of LMW on the expression of ang-2 was observed. Ang-2 is one of the crucial proteins involved in angiogenesis: it is implicated in vessel maturation and facilitates endothelial cell responsiveness to angiogenic and inflammatory stimuli. Thus, it seems that EMD proteins with different molecular weights affect the ang-2 expression differently.

It was found that the expression of vWF is up-regulated by EMD and LMW. In contrast, no significant effect of LMW-depleted on vWF expression was observed. vWF is involved in the platelet adhesion, and platelet, in turn, might release several factors supporting angiogenesis and wound healing. The present results suggest that low molecular weight EMD proteins are involved in inducing vWF gene expression in endothelial cells. Interestingly, vWF production in endothelial cells is controlled by KDR. It stands to reason that the increase of vWF expression is directly linked to the up-regulation of KDR expression by LMW.

The ability of EMD to stimulate migration of endothelial cells was shown by several previous reports. Endothelial cell migration is one of the key processes in angiogenesis. In the present study it was found that EMD fractions LMW and LMW-depleted possess different chemotactic activity. The migration of HUVECs measured using a chemotaxis chamber was strongly stimulated by LMW and this effect was markedly higher than that of LMW-depleted. Similarly, the migration of HUVECs measured in time lapse microscopy experiments was more strongly stimulated by LMW than LMW-depleted. It is known that endothelial cells migration is stimulated by activation of VEGF receptor 2 (KDR). Therefore, it is likely that high chemotactic activity of LMW could be due to activation of KDR expression in HUVECs. Stimulation of HUVECs migration by LMW suggests that proteins of this EMD fraction are important for migration of endothelial progenitor cells into the wounded area, which is a pre-requisite for vessel formation.

Wound healing is a complicated process which consists of different phases that overlap in time: inflammation, tissue formation, and tissue remodelling. Angiogenesis plays an important role in all phases of wound healing: hemostatic clot formation provides a provisional matrix for tissue formation; blood vessels supply nutrients and oxygen and facilitate access of inflammatory cells to the wound. The present data suggest that the functional parameters of HUVECs, which might be potentially involved in wound healing and angiogenesis, are differently affected by different EMD fractions which have different effects on the migration and the expression of different proteins in HUVECs. Particularly, proteins with a molecular weight >8 kDa seem to stimulate the inflammatory phase of wound healing, which is implied by the strong up-regulation of adhesion molecules E-selectin and ICAM-1 by LWM-depleted. EMD proteins with a molecular weight <8 kDa stimulate the expression of VEGF receptors and vWF, as well as cell migration, and are involved in the tissue formation phase of wound healing process. However, the presence of proteins from both LMW and LMW-depleted are important for biological of EMD. This knowledge can be used for the development of new systems, in which release of bioactive components from EMD is regulated in time. Such approach can specifically enhance different phases of wound healing process and therefore improve therapy outcome.

In summary, the present data clearly demonstrates that EMD proteins with different molecular weights possess noticeable different biological activities on endothelial cells and vessels. This finding provides an important basis for the development of new EMD-related products with high clinical effectivity, biocompatibility, and potentially lower costs Experiment 2

Introduction

EMD (enamel matrix derivative) is extracted from developing porcine teeth and has been shown to play a key role in the development of tooth-supporting tissues (periodontium). EMD can be separated into a number of sub-fractions by size-exclusion and reverse-phase HPLC. In this report two complementary fractions are described called Low Molecular Weight (LMW) and Low Molecular Weight depleted (LMWdepl), how they were produced, identified and characterized.

Both EMD fractions LMW and LMW-depl were always isolated from the EMD lot 632A (EMD 632A; heat treated). Protein components of these fractions were identified by MS analysis at the Protein Analysis Facility (PAF), University Lausanne, headed by Dr. M. Quadroni.

Material and Methods

Isolation of EMD Fraction LMW and LMW-Depl

Size exclusion chromatography (SEC) of EMD 632A was done using a preparative Shodex KW 2003 column (Shodex, marketed in Switzerland by Brechbühler A G, dimensions 300×20.0 mm) packed with porous spherical silica gel covered with hydrophobic chemically-bound hydroxyl groups on an ÄKTApurifier core system (GE Healthcare) including a pH/C-900 monitor. In a single run 500 µl corresponding to 15 mg EMD were applied to the column by manual injection through a 500 µl-loop using a syringe. EMD was fractionated using 100 mM Na acetate pH 3.53 containing 100 mM NaCl as eluent at a flow rate of 2 ml/min. Elution of protein was followed spectrophotometrically at 280 nm. Normally multiple runs a 15 mg each were conducted and corresponding fractions LMW and LMW-depl, respectively, pooled and lyophilized.

2.2 SDS-PAGE
2.3 Protein Determination
2.4 Maldi TOF/TOF, LC-MS and Analysis
3. Results and Discussion
3.1 Isolation of EMD Fraction LMW and LMW-Depl by HPLC EMD separation by SEC-HPLC on a preparative silica gel column leaded to 7 major peaks (FR0277, FR0282). In FIG. 8 a representative chromatogram is shown. LMW-depleted was collected between a retention time ($t_R$) of 16 min to 18 min and 13 min to 38 min while LMW was collected between $t_R$=38 min to 46 min as indicated.

LMW-depleted contained the largest peak including a shoulder found in the whole EMD profile representing the main protein component of EMD, the 20 kDa amelogenin. The profile of LMW consisted of one large peak at a $t_R$ of approximately 43 min which was later identified as TRAP-63. Two other isolated peaks were observed as well as three smaller ones which were not well separated. Over the course of 3 years, this profile was reproduced multiple times and it is therefore safe to assume that EMD fraction LMW from different isolations (if stemming from EMD 632A) is similar enough to be used in in vitro (biochemistry and cell biology) and in vivo experiments (eg LMW coated bone graft particles).

3.2 SDS-PAGE Analysis of EMD Fraction LMW and LMW-Depl

The mass distribution of the EMD proteins in fractions LMW and LMW-depl was checked by SDS-PAGE (FIG. 9). Proteins of a molecular weight 8 kDa were mostly found in fraction LMW while proteins with a molecular mass above 8 kDa and especially around 20 kDa were mostly if not uniquely components of fraction LMW-depl. The protein profiles of EMD632A, fraction LMW and fraction LMW-depleted corresponded to protein profiles found in previous studies. LMW contained significantly less of the 20 kDa amelogenin than fraction LMW-depl. The main proteins in LMW were represented by two protein bands at about 5 kDa and 7 kDa. It is noteworthy that the small amelogenin compounds (3-8 kDa) like LRAP and TRAP were separated from the larger mass proteins very nicely by the fractionation of EMD into fractions LMW and LMW-depleted.

3.3 LC-MS of EMD Fraction LMW and LMW-Depl

Protein components in EMD fractions LMW and LMW-depl were identified by LC-MS conducted by Dr. M. Quadroni at the Uni Lausanne. In FIG. 10 protein bands observed on SDS-PAGE gels of LMW and LMW-depleted are indicated with the corresponding identification. The two proteins bands at 5 kDa and approximately 7 kDa in LMW contained a lot of different short amelogenin peptides. Most of them consisted of the 27 to 51 N-terminal amino acids from amelogenin. Hemoglobins found in EMD fractions were contaminations stemming from the acidic protein extraction of developing porcine tooth buds. The majority of the 20 kDa amelogenin (the main protein in EMD) was found in EMD fraction LMW-depleted. Ameloblastin was mainly detected in fraction LMW-depleted whereas hemoglobin □ and enamelin were found in both fractions. It is worth noting that short amelogenin peptides like extended TRAP (=TRAP-63) and TRAP-43/45 were solely detected in fraction LMW.

3.4 MALDI TOF/TOF Analysis

Fraction LMW

Figure 11A:
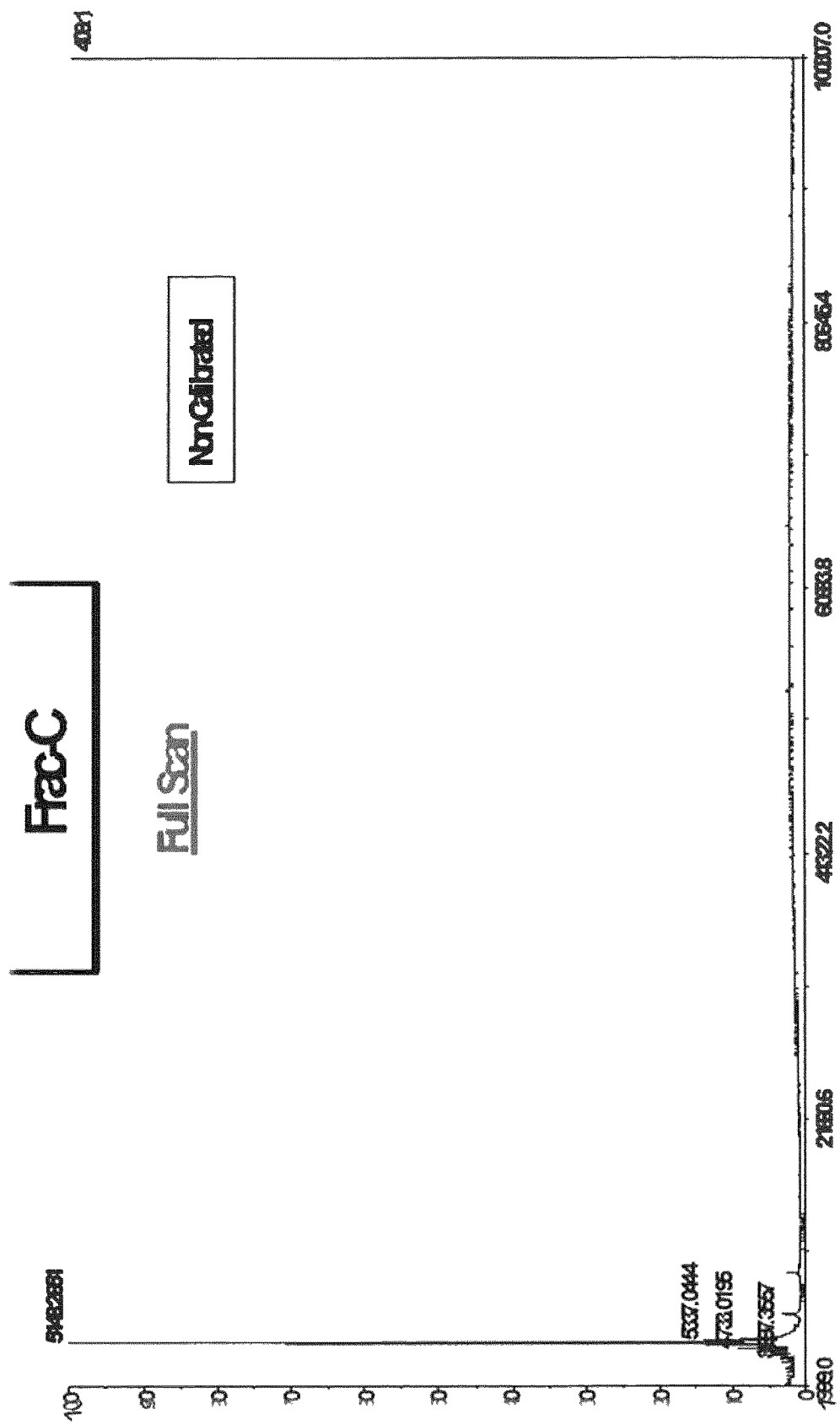
Figure 11B:
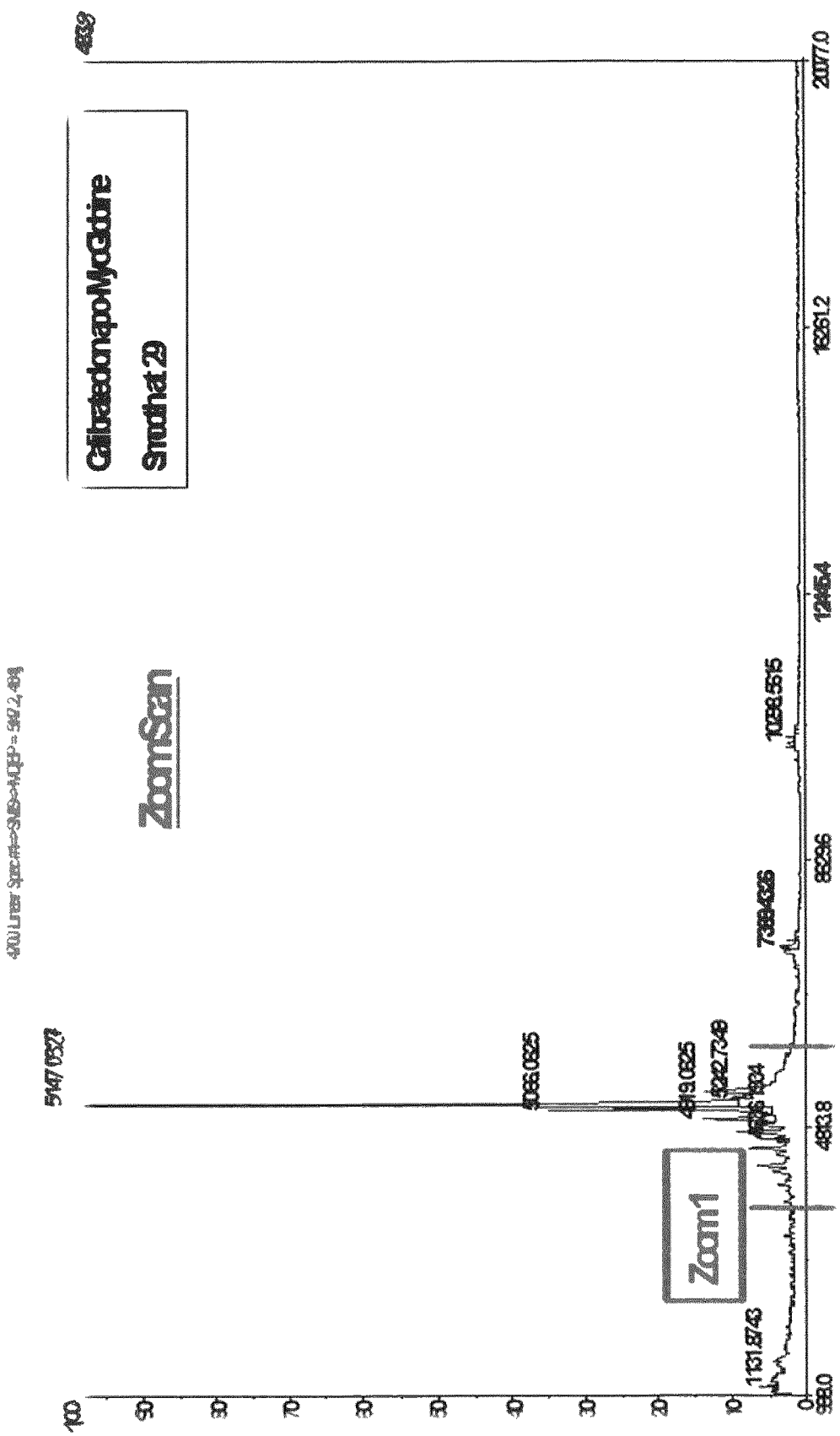
Figure 11C:
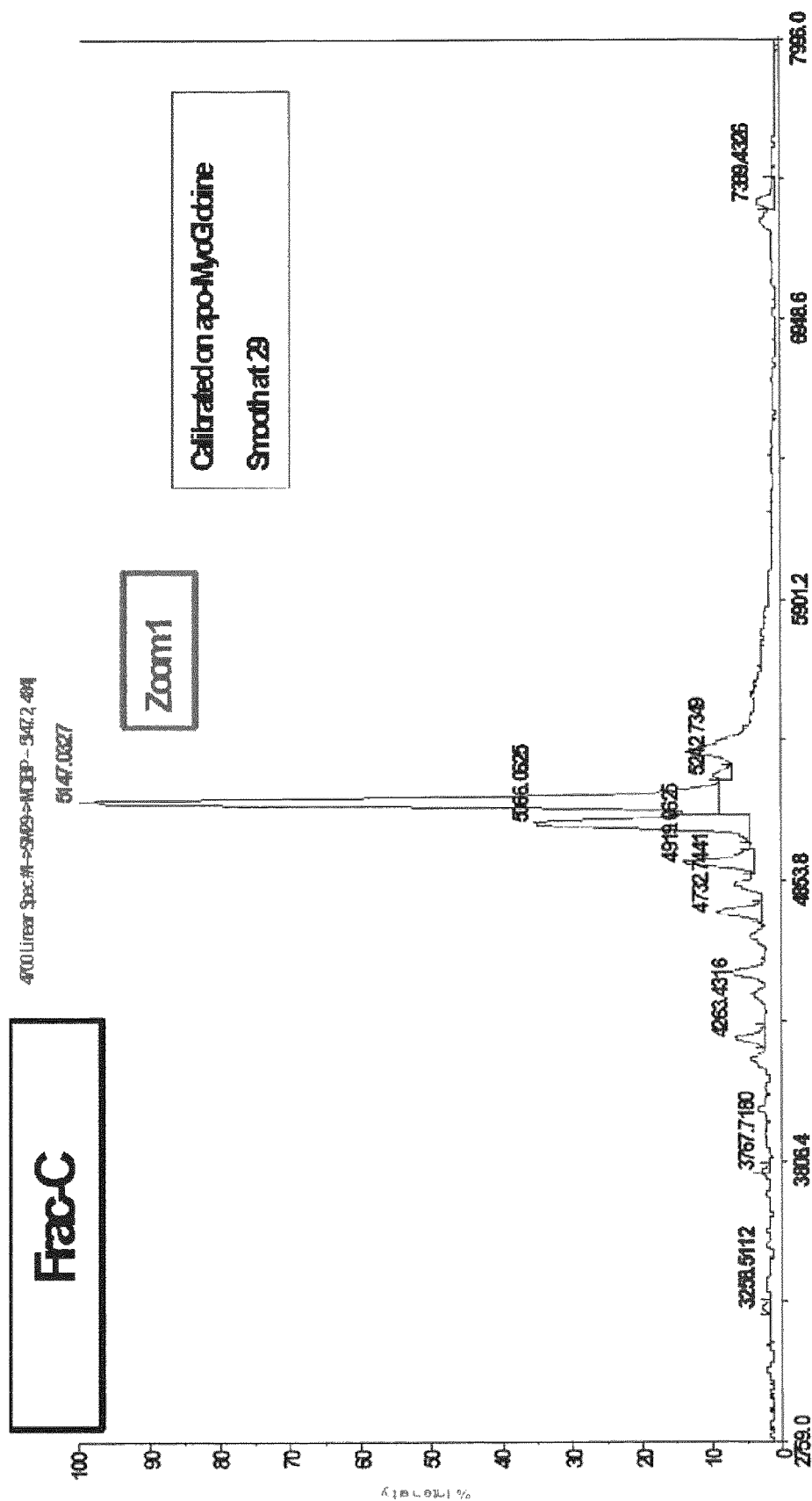
Figure 12A:
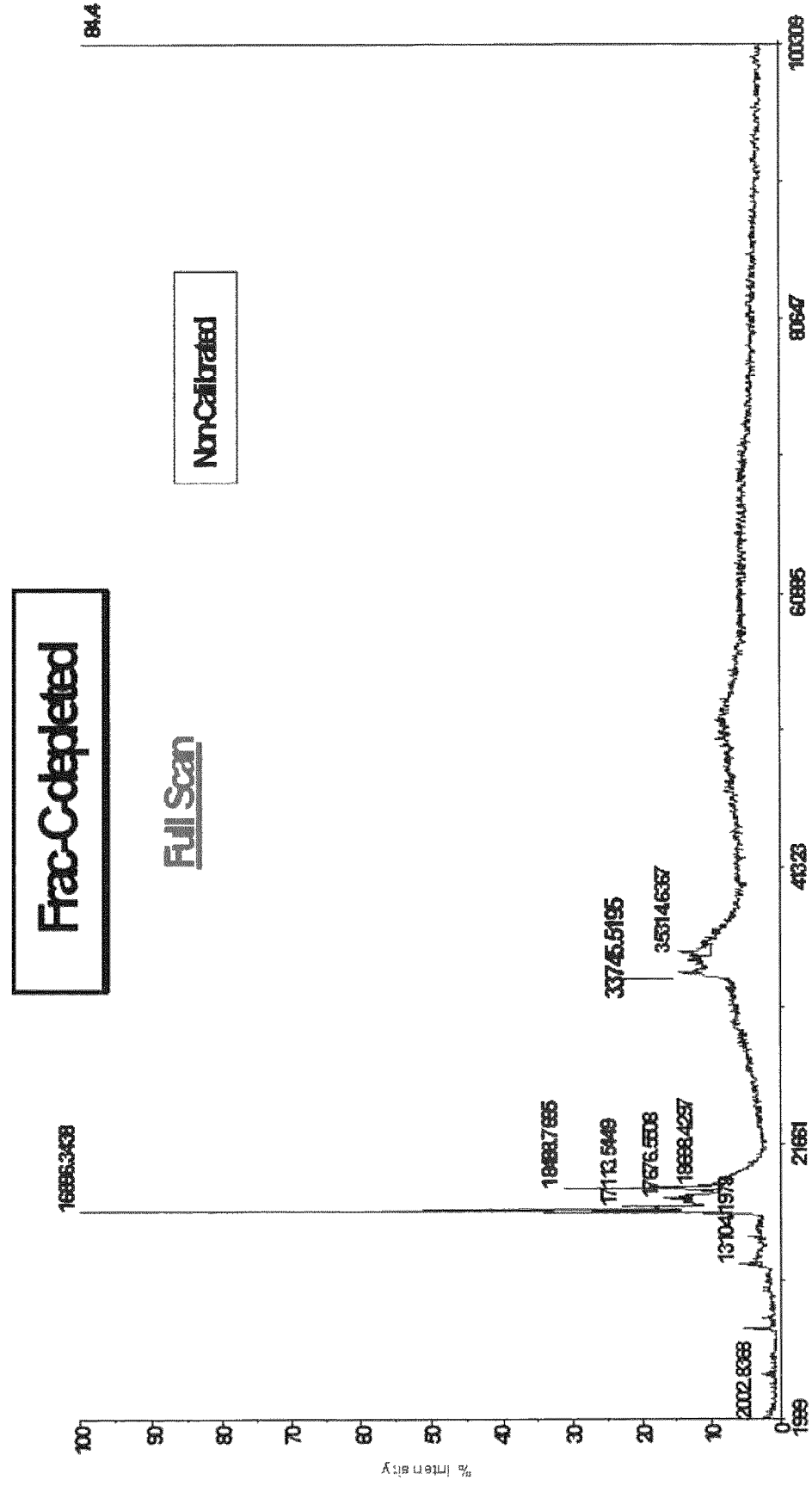
Figure 12B:
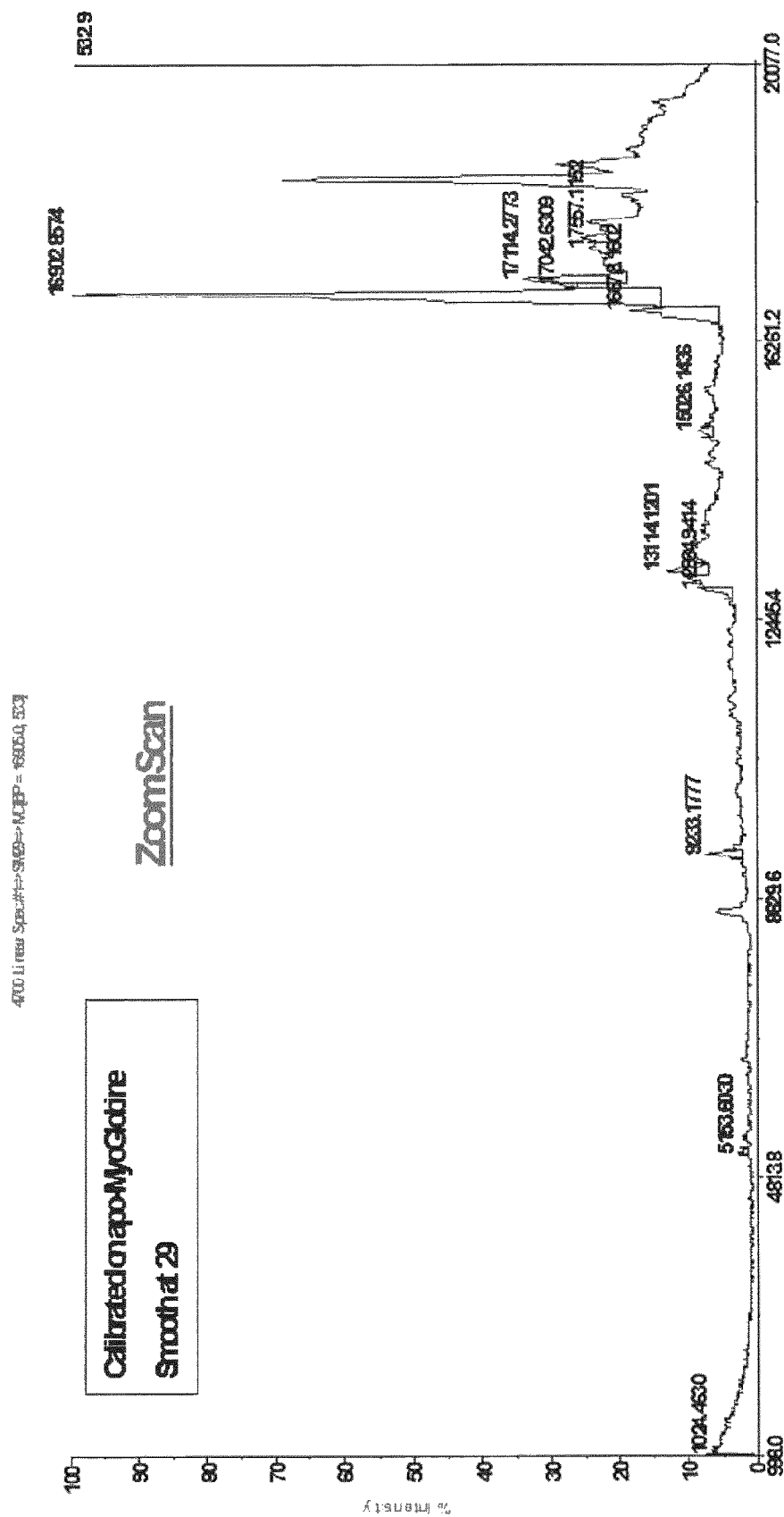

TRAP-43 was observed at a mass of 5148.2651 as expected (FIG. 11). However, LRAP (full length LRAP-56) at a calculated protein mass of 6.5 kDa (phosphorylated 6.6 kDa) was not detected. It is believed that full length LRAP degrades immediately after extraction and only C-terminally truncated LRAP species can be observed. LRAP-45 (5.3 kDa) and LRPA-49 (5.7 kDa) (full length: LRAP-56) were identified. The small peak seen at 7389.4326 is TRAP-63 (expected 7412 for phosphorylated TRAP-63). The peak at 10298 is the double size peak from TRAP-43. The SDS-PAGE analysis shows very clearly that there must be a protein of a mass around 6-7 kDa in fraction LMW. Zoom 1 (FIG. 12) shows numerous small peptide masses that might come from amelogenin degradation products. It is noteworthy that no mass corresponding to the 20 kDa amelogenin was detected. This protein was detected by SDS-PAGE only in insignificant amounts (FIG. 9).

Fraction LMW-Depleted

In FIG. 9 none of the characteristic peaks between 5100 and 5400 was detected. This was to be expected as in the SDS-PAGE analysis (FIG. 9) no protein bands of a mass smaller than 8 kDa were observed. Peaks representing the 20 kDa (16896.3438) and the 23 kDa (18698.4297) amelogenin were seen, as well as many more peaks around this mass area which might represent amelogenin species with a different number of amino acids. Interestingly, for the first time also peak at larger masses of 33745 and 35314 were detected. Pig enamelin species of 32 kDa and 34 kDa size have been described.

REFERENCE LISTING

1. Gestrelius S, Lyngstadaas S P, Hammarstrøm L. Emdogain—periodontal regeneration based on biomimicry. Clin Oral Invest 4:120-125 (2000)
2. Hammarström et al., 1997, Journal of Clinical Periodontology 24, 658-668
3. Lyngstadaas et al., 2001, Journal of Clinical Periodontology 28, 181-188
4. U.S. Pat. No. 4,672,032
5. EP-B-0 337 967
6. EP-B-0 263 086
7. EP-1059934
8. EP-01201915.4
9. WO 01/97834
10. WO 00/53197
11. WO 00/53196
12. WO 03/024479
13. WO 02/080994
14. Boabaid F., et al, J. Periodontol, Vol 75, No. 8, 2004
15. WO 2009/157869
16. Dayhoff, Schwartz, and Orcutt (1978) Atlas Protein Seq. Struc. 5:345-352
17. Henikoff and Henikoff (1992) Proc Natl Acad Sci USA 89(22):10915-9
18. Simon R J et al., PNAS (1992) 89(20), 9367-9371 and Horwell D C, Trends Biotechnol. (1995) 13(4), 132-134
19. Sambrook, J. et al.: Molecular Cloning, Cold Spring Harbor Laboratory Press, 1989
20. Ten Cate: Oral Histology, 1994; Robinson: Eur. J. Oral Science, January 1998, 106 Suppl. 1:282-91
21. BLAST Manual, Altschul, S. F. et al, Altschul, S. F. et al (1990)
22. "Remington's Pharmaceutical Sciences", 18th Edition, Mack Publishing Company, Easton, 1990
23. "Encyclopedia of Pharmaceutical Technology", edited by Swarbrick, J. & J. C. Boylan, Marcel Dekker, Inc., New York, 1988
24. Qu Z, Laky M, Ulm C, Matejka M, Dard M, Andrukhov O, Rausch-fan X. Effect of Emdogain on proliferation and migration of different periodontal tissue-associated cells. Oral Surg Oral Med Oral Pathol Oral Radiol Endod 2010; 109(6):924-31
25. Andrukhov O, Steiner I, Liu S, Bantleon H P, Moritz A, Rausch-Fan X. Different effects of *Porphyromonas gingivalis* lipopolysaccharide and TLR2 agonist Pam3CSK4 on the adhesion molecules expression in endothelial cells. Odontology 2014.
26. Pasceri V, Willerson J T, Yeh E T. Direct proinflammatory effect of C-reactive protein on human endothelial cells. Circulation 2000; 102(18):2165-8.

The invention claimed is:

1. A pharmaceutical composition which stimulates the tissue formation phase of a wound healing process, said composition comprising a mixture of enamel matrix polypeptides and/or proteins with a molecular weight <8 kDa, wherein said mixture is free of enamel matrix polypeptides and/or proteins with a molecular weight >8 kDa, and a suitable pharmaceutical carrier, wherein said mixture comprises the enamel matrix polypeptide of SEQ ID NO: 1 (TRAP63).

2. A pharmaceutical composition according to claim 1, wherein the mixture further consists of one or more enamel matrix polypeptides selected from the group of enamel matrix polypeptides consisting of:
   a. SEQ ID NO: 2 (TRAP43),
   b. SEQ ID NO: 3 (TRAP45), and
   c. SEQ ID NO: 4 (LRAP56).

3. A pharmaceutical composition according to claim 1, comprising at least one of said enamel polypeptides is produced by synthesis in vitro.

4. A pharmaceutical composition according to claim 3, wherein the pharmaceutically acceptable carrier is selected from the group consisting of PGA and PEG.

5. A pharmaceutical composition according to claim 1, comprising at least one of said enamel polypeptides that is a purified recombinant polypeptide fragment.

6. A pharmaceutical composition according to claim 1, wherein at least one of said enamel polypeptides is synthetically and/or chemically altered.

7. A pharmaceutical composition according to claim 1, comprising at least one of said enamel polypeptides produces by synthesis in vivo.

8. A pharmaceutical composition according to claim 1, further comprising EMD.

9. A method of accelerating onset of wound healing comprising administering an enamel matrix polypeptide according to claim 1 to a subject suffering from a wound, in an amount sufficient to accelerate onset of wound healing.

10. A method of accelerating wound healing, comprising administering an enamel matrix polypeptide according to claim 1 to a subject suffering from a wound in an amount sufficient to accelerate wound healing.

11. A method of treating an inflammatory condition, comprising administering a therapeutically effective amount of an enamel matrix polypeptide according to claim 1 to a subject suffering from an inflammatory condition.

12. A method of promoting periodontal soft tissue generation, comprising administering, to a subject in need of such treatment, an enamel matrix polypeptide according to claim 1 in an amount sufficient to promote periodontal soft tissue regeneration.

13. A method of stimulating angiogenesis, comprising administering an enamel matrix polypeptide according to claim 1 to a subject in an amount sufficient to generate angiogenesis.

14. A pharmaceutical composition which stimulates the tissue formation phase of a wound healing process, said composition comprising an acid-extraction of enamel proteins and/or polypeptides derived from developing mammalian tooth buds, which is at least 2× enriched in an enamel matrix polypeptide which has the amino acid sequence as shown in SEQ ID NO: 1 (TRAP63), or a pharmaceutically acceptable salt thereof.

15. A process for producing an enamel matrix polypeptide which has the amino acid sequence as shown in SEQ 10 NO: 1 (TRAP63), a homologue, analogue, or a pharmaceutically acceptable salt thereof, which stimulates the tissue formation phase of wound healing process, comprising:
   a. Isolating the enamel proteins present in a defined amount of developing animal tooth buds, and
   b. Removing any protein with a molecular weight (M.W.) >8 kDa from said isolate.

16. A process according to claim 15, wherein the enamel polypeptides are isolated from human, porcine, bovine, rat, mouse and/or sheep developing tooth buds.

17. A pharmaceutical composition comprising proteins with a molecular weight (M.W.)<8 kDa, wherein said composition is produced according to the process of claim 15.

* * * * *